United States Patent

Yoshimura et al.

[11] Patent Number: 5,831,178
[45] Date of Patent: Nov. 3, 1998

[54] VIBRATION TYPE MEASURING INSTRUMENT

[75] Inventors: Hiroyuki Yoshimura, Kanagawa; Takahiro Kudo; Masami Kishiro, both of Tokyo, all of Japan

[73] Assignee: Fuji Electric Co., Ltd.

[21] Appl. No.: 705,343

[22] Filed: Aug. 29, 1996

Related U.S. Application Data

[63] Continuation-in-part of Ser. No. 525,466, Sep. 8, 1995, Pat. No. 5,728,952.

[30] Foreign Application Priority Data

Aug. 29, 1995 [JP] Japan .................................. 7-220128
Dec. 22, 1995 [JP] Japan .................................. 7-333837

[51] Int. Cl.$^6$ ...................................................... G01F 1/84

[52] U.S. Cl. ............................... 73/861.357; 73/861.356

[58] Field of Search ........................ 73/861.356, 861.357

[56] References Cited

U.S. PATENT DOCUMENTS

| | | | |
|---|---|---|---|
| 4,680,974 | 7/1987 | Simonson et al. ................... | 73/861.357 |
| 4,801,897 | 1/1989 | Flecken ............................... | 73/861.357 |
| 5,024,104 | 6/1991 | Dames ................................. | 73/861.357 |
| 5,054,326 | 10/1991 | Mattar ................................. | 73/861.38 |
| 5,115,683 | 5/1992 | Pratt ................................... | 73/861.38 |
| 5,321,991 | 6/1994 | Kalotay ............................... | 73/861.357 |
| 5,373,745 | 12/1994 | Cage ................................... | 73/861.37 |
| 5,398,554 | 3/1995 | Ogawa et al. ....................... | 73/861.38 |
| 5,448,921 | 9/1995 | Cage et al. .......................... | 73/861.38 |
| 5,469,748 | 11/1995 | Kalotay ............................... | 73/861.38 |

FOREIGN PATENT DOCUMENTS

| | | | |
|---|---|---|---|
| 0698783 | 2/1996 | European Pat. Off. ........... | G01F 1/84 |
| 8911275 | 3/1990 | France ............................... | G01F 1/84 |
| 4224379 | 12/1993 | Germany ........................... | G01F 1/84 |
| 19525253 | 1/1996 | Germany ........................... | G01F 1/84 |
| 3923409 | 1/1996 | Germany ........................... | G01F 1/84 |
| 19634663 | 8/1996 | Germany ........................... | G01F 1/84 |
| 569452 | 5/1993 | Japan ................................. | G01F 1/84 |
| 6-94501 | 4/1994 | Japan ................................. | G01F 1/84 |
| 663958 | 6/1994 | Japan ................................. | G01N 9/00 |
| 8706691 | 11/1987 | WIPO ................................. | G01F 1/84 |
| 8802477 | 4/1988 | WIPO ................................. | G01F 1/84 |
| 8802853 | 4/1988 | WIPO ................................. | G01N 9/00 |
| 8900679 | 1/1989 | WIPO ................................. | G01F 1/84 |

*Primary Examiner*—Ronald L. Biegel
*Assistant Examiner*—Harshad Patel
*Attorney, Agent, or Firm*—Elman & Associates

[57] ABSTRACT

A vibration type measuring instrument measures at least one of a mass flow rate and a density of a fluid flowing through a straight measurement pipe by vibrating the measurement pipe, obtains a frequency ratio of a resonant frequency of a first vibration mode to a resonant frequency of a second vibration mode of the measurement pipe, and corrects a measured value of at least one of the mass flow rate and the density according to the frequency ratio. The instrument includes a first vibration detector for detecting at least one of a vibration generated in the measurement pipe depending on the mass flow rate and the resonant frequency of the first vibration mode of the measurement pipe; and a second vibration detector for detecting the resonant frequency of the second vibration mode of the measurement pipe. The second vibration detector is provided around an antinode of the second vibration mode of the measurement pipe to improve the detection sensitivity in the second vibration mode.

9 Claims, 15 Drawing Sheets

VIBRATION TYPE MEASURING INSTRUMENT

CROSS REFERENCE TO RELATED APPLICATION

This application is a continuation-in-part application of U.S. patent application Ser. No. 08/525,466 filed on Sep. 8, 1995, now U.S. Pat. No. 5,728,952, which is incorporated by reference in this application.

BACKGROUND OF THE INVENTION

1. Field of the Invention

The present invention relates to a mass flowmeter for fluid for measuring a mass flow (mass flow rate) based on the Coriolis force generated by the mass flow of the fluid flowing through a measurement pipe by vibrating the measurement pipe, to a vibration density meter for measuring the density of the fluid depending on the variation of the resonant frequency of the measurement pipe which varies according to the density of the fluid in the above described measurement pipe, and to a vibration type measuring instrument having the functions of both of the above described meters, and especially to the vibration type measuring instrument and vibration measuring instrument adjusting device capable of adjusting or correcting a measured value depending on the fluid temperature, atmospheric temperature, and axial force (stress).

DESCRIPTION OF THE RELATED ART

FIG. 1 shows a configuration of an example of a straight-pipe type mass flowmeter.

A detecting unit 1 of the flowmeter comprises a straight measurement pipe 2; right and left fixtures 3a and 3b for fixing the node portions a and b of the vibration of the measurement pipe 2; supporters 4a and 4b (only 4a is shown in FIG. 1) fixed to the fixtures 3a and 3b with screws or by soldering, etc., or designed as being combined with the fixtures 3a and 3b so that the vibrations of the fixtures 3a and 3b cancel each other; and a vibration generator 5, comprising coils fixed to the supporters 4a and 4b by an adapter 7a and a magnet fixed to the central portion of the measurement pipe 2, for vibrating the measurement pipe 2 at its resonant frequency.

The detecting unit 1 further comprises, similar to the vibration generator 5, speed detecting sensors (or displacement sensors or acceleration sensors) 6a and 6b, comprising magnets fixed symmetrically about the vibration generator 5 on the measurement pipe 2, with coils fixed to the supporters 4a and 4b by the adapters 7b and 7c, for detecting the vibration of the measurement pipe 2; a drive circuit 8 for receiving an output from the speed detecting sensor 6a and outputting a drive signal to the vibration generator 5 so that the signal amplitude can be kept constant; and a signal processing circuit 9 for outputting a mass flow signal Qm based on the phase difference (time difference) of the signals from the speed detecting sensors 6a and 6b.

Assume that the flow of the fluid is zero in the detecting unit 1 designed as described above.

The measurement pipe 2 is vibrated at its resonant frequency by the vibration generator 5, speed detecting sensor 6a and drive circuit 8. Since the speed detecting sensors 6a and 6b are mounted symmetrically about the center of the measurement pipe 2, signals of equal amplitude can be obtained without phase difference from the speed detecting sensors 6a and 6b.

If the fluid flows through the vibrating measurement pipe 2, the speed component in the vibration direction is increased as shown in FIG. 2, as the fluid flows from the node a of the measurement pipe 2 toward the center of the measurement pipe 2. Therefore, the fluid flowing through the measurement pipe 2 receives positive acceleration from the measurement pipe 2 in the vibration direction. As a result, the reaction of the fluid acts on the measurement pipe 2, and the phase of the vibration is retarded between the node a of the measurement pipe 2 and the center of the measurement pipe 2, as shown in FIG. 3. Since the speed component in the vibration direction is decreased as the fluid flows from the center of the measurement pipe 2 to the node b, the fluid flowing through the measurement pipe 2 receives negative acceleration (retardation) from the measurement pipe 2 in the vibration direction. As a result, the reaction of the fluid acts on the measurement pipe 2, and the phase of the vibration is advanced between the center of the measurement pipe 2 and the node b of the measurement pipe 2, as shown in FIG. 3.

The displacement variation in the measurement pipe 2 is described by referring to the following equations.

The displacement of the measurement pipe 2 at the displacement sensor 6a is represented by the following equation, according to the displacement of the transverse vibration of the measurement pipe 2 through resonance.

$$Ya = \eta(a)\sin\omega_n t \quad (1)$$

where $\eta(a)$: function indicating the amplitude of a position a in the axial direction of the measurement pipe 2

$\omega_n$: resonant frequency of the measurement pipe 2.

The deformation (displacement, or deflection) of the measurement pipe 2 caused by the reaction of the fluid on the displacement sensor 6a is represented by the following equation.

$$ya = \{-2L^3 \, Qm \, \omega_n \, \eta c(a)\cos\omega_n t\}/EI \quad (2)$$

where

L: length of the measurement pipe 2

E: Young's modulus for the measurement pipe 2

I: Sectional secondary moment of the measurement pipe 2

Qm: mass flow rate of fluid in the measurement pipe 2

$\eta c(a)$: deformation amplitude function of the measurement pipe 2 according to the reaction from the fluid at the position a in the axial direction of the measurement pipe 2.

The actual deformation of the measurement pipe 2 is determined by superposing the deformation of the measurement pipe 2 as calculated by equation (2) onto the deformation of the measurement pipe 2 caused through resonance calculated by equation (1). That is, the total deformation (displacement) of the measurement pipe 2 is calculated by equation (3) which is a combination of equations (1) and (2).

$$\xi a = Ya + ya = A \sin(\omega_n t - \alpha) \quad (3)$$

where $$A = [\eta(a)^2 + \{2L^3 \, Qm \, \omega_n \, \eta c(a)/EI\}^2]^{1/2} \quad (4)$$

$$\alpha = 2L^3 Qm \, \omega_n \, \eta c(a)/EI\eta(a) \quad (5)$$

Since the displacement sensors 6a and 6b are mounted symmetrically about the center of the measurement pipe 2, the displacement of the transverse vibration of the measurement pipe 2 in the displacement sensor 6b is equal to the displacement in the displacement sensor 6a. That is;

$$Yb = Ya = \eta(a)\sin\omega_n t \qquad (6)$$

Since the value of the reaction of the fluid on the displacement sensor 6b on the measurement pipe 2 is equal to that of the fluid on the displacement sensor 6a in the opposite direction, the following equation is defined.

$$yb = -ya = \{2L^3 \, Qm \, \omega_n \, \eta c(a)\cos\omega_n t\}/EI \qquad (7)$$

Therefore, the deformation of the measurement pipe 2 is calculated by the following equation.

$$\xi b = Ya - ya = A \sin(\omega_n t + \alpha) \qquad (8)$$

According to equations (3) and (8) above, a phase difference of $2\alpha$ exists between the signals of the displacement sensors 6a and 6b. Equation (5) indicates that the phase difference of $2\alpha$ is proportional to the mass flow rate Qm. Therefore, the time difference between the signals of the displacement sensors 6a and 6b is calculated by the following equation.

$$\Delta t = 2\alpha/\omega_n = 4L^3 \, Qm \, \eta c(a)/EI\eta(a) \qquad (9)$$

The resonant frequency of the measurement pipe 2 is calculated by the following equation.

$$\omega_n = \lambda^2/L^2 \cdot (EI/\rho)^{1/2} \qquad (10)$$

where $\lambda$: constant depending on the boundary conditions and vibration mode of the measurement pipe 2

$\rho$: line density including the measurement pipe 2 and the fluid in the measurement pipe 2.

If the temperature of the measurement pipe 2 changes, the phase and time differences between sensor output signals also change because of the temperature-dependency of Young's modulus E according to equations (5) or (9), even if the mass flow rate Qm is constant. Similarly, even though no density change is detected in the fluid to be measured, the resonant frequency $\omega_n$ in equation (10) changes with temperature.

In the above description, the axial force (stress) working on the measurement pipe 2 has not been considered. However, considering the influence of axial force, the function n indicating the amplitude of the measurement pipe 2 indicates not only the position of the measurement pipe 2 but also a function of the axial force T. Therefore, the above described equation (1) can be represented as follows.

$$Ya = \eta(a, T)\sin\omega_n t \qquad (11)$$

Further, the above listed equations (5) and (9) can be represented as the following equations.

$$\alpha = 2L^3 \, Qm \, \omega_n \, \eta c(a, T)/EI\eta(a, T) \qquad (12)$$

$$\Delta t = 2\alpha/\omega_n = 4L^3 \, Qm \, \eta c(a, T)/EI\eta(a, T) \qquad (13)$$

That is, the phase and time differences generated in proportion to the mass flow rate depend on the axial force working on the measurement pipe 2. At this time, the resonant frequency $\omega_n$ of the measurement pipe 2 can be calculated by the following equation.

$$\omega_n = \lambda_n(T)^2/L^2 \cdot (EI/\rho)^{1/2} \qquad (14)$$

The resonant frequency $\omega_n$ of the measurement pipe 2 also refers to a function of the axial force working on the measurement pipe 2.

Normally, the mass flowmeter measures the mass flow rate based on the Coriolis force generated by the mass flow rate of the fluid through the vibrating measurement pipe 2. If the temperature of the measurement pipe 2 changes with a variation in the temperature of the object fluid or the atmospheric temperature, the rigidity of the measurement pipe 2 changes with the temperature-dependency of Young's modulus for the measurement pipe 2, thereby changing the sensitivity to the Coriolis force and the measured flow value. If a Coriolis-type mass flowmeter having a straight measurement pipe is used, the axial force working on the measurement pipe changes with the expansion or contraction of the measurement pipe 2 and supporters 4a and 4b, because of the above described change in temperature. A change in the axial force also changes the sensitivity of the mass flow rate measurement.

Similarly, with the vibrating density meter, if the temperature of the measurement pipe 2 changes with a variation of the temperature of the object fluid or the atmospheric temperature, the resonant frequency changes with the temperature-dependency of Young's modulus for the measurement pipe 2, thereby generating erroneous measurements. Especially, with the measurement pipe 2, the resonant frequency changes with the variation of the axial force working on the measurement pipe 2, generating erroneous measurements.

As described above, amendments may be made according to the technologies disclosed in the Japanese Patent Publication No. 5-69452, and corresponding U.S. Pat. No. 4,768,384, and the Japanese Laid-open Patent Publication No. 6-94501, when the sensitivity and measured values of the mass flowmeter change with variations in environmental temperature.

According to the former publication, two temperature sensors are mounted on portions in supporters indicating a temperature identical to that of the measurement pipe 2. The signals from the two temperature sensors are input to a correction circuit, and the flow rate signals from the two vibration sensors are also input to the correction circuit for correction.

According to the latter publication, the measured flow value is corrected corresponding to the temperature of the measurement pipe 2. To attain this, the system includes a temperature sensor for detecting the temperature of the measurement pipe 2, and a length change sensor (for example, a deformation gauge such as a strain gauge) for correcting a measured value depending on the length and stress of the measurement pipe 2, and each signal is input to a correction circuit.

If the temperature of the measurement pipe 2 and the supporters is measured, and changes according to the change in Young's modulus and the axial force on the measurement pipe 2 are estimated indirectly, as shown in the former publication, different temperature gradients appear in the measurement pipe 2, depending on the difference between the fluid temperature and the environmental temperature, even when the temperatures themselves are stable. If the fluid temperature and environmental temperature are in a transitional state, each of the temperature gradients changes. Therefore, the temperature measurement point at which an average temperature of the measurement pipe 2 and supporters can be obtained changes in the above described states, and therefore measured values may not be corrected appropriately at a specific point.

If the deformation of the measurement pipe 2 is directly measured, as in the latter publication, accurate deformation correction can be performed. However, because it is necessary to fix a strain gage and the like directly to the measurement pipe 2, the vibration characteristics of the measurement pipe 2 may be adversely affected, this produces a problem with the stability of measurement.

To avoid this undesired influence, a mass is mounted on each side of the measurement pipe 2, and a strain gauge is applied to the outer side of the mass. In this case, the volume of the mass must be large with respect to the measurement pipe 2, generating another problem that the mass flow meter becomes large and heavy.

There is another configuration in which a strain gauge is applied to the supporters. However, since the rigidity of the supporters must be large enough to allow stable vibration of the measurement pipe, the sectional area of the measurement pipe is much smaller than that of the supporters, and the deformation generated on the supporters and is much smaller than that on the measurement pipe. Therefore, there is a problem of a large error in the method of estimating the deformation on the measurement pipe, based on the deformation of the supporters. Although an embodiment of measuring the length of the measurement pipe with a length change lot is disclosed, the structure is too complicated to be considered acceptable.

As clearly indicated by the above described equation (14), the resonant frequency of the measurement pipe varies with a change in the axial force (stress) T. Since the variations caused by the change in the axial force of $\lambda_n(T)$ determined by the boundary condition and vibration mode are dependent on each vibration mode, the resonant frequency ratio of each vibration mode changes with the change in a working axial force.

FIGS. 4A and 4B show the ratio of the basic mode resonant frequency to the second-mode resonant frequency when the axial force working on the measurement pipe changes, and the ratio of the basic mode resonant frequency to the third-mode resonant frequency, respectively. As shown in these figures, the resonant frequency ratio between the modes changes almost linearly. This holds true with the resonant frequency ratio between optional modes.

This indicates that the axial force working on the measurement pipe can be obtained by measuring the resonant frequency ratio between the modes. The Applicants carefully considered this and have already filed an application about a method of adjusting the change in flow rate measurement sensitivity and the measured density value which vary with a change in the axial force working on the measurement pipe (Japanese Patent Application No. 6-215663, U.S. patent Ser. No. 08/525,466).

However, there is room for improvement in the above described application.

SUMMARY OF THE INVENTION

The present invention aims at improving the measurement precision by adjusting or correcting a change in the flow rate measurement sensitivity and measured density value, which vary according to a change in the axial force working on the measurement pipe, according to the resonant frequency ratio.

A vibration type measuring instrument according to the present invention measures at least one of a mass flow rate and a density of a fluid flowing through a straight measurement pipe by vibrating the measurement pipe, obtains a frequency ratio of the resonant frequency of (in) the first vibration mode to the resonant frequency of the second vibration mode of the measurement pipe, and corrects a measured value of at least one of the mass flow rate and the density according to the frequency ratio.

The first vibration type measuring instrument according to the present invention comprises; the measurement pipe; a first vibration detector for detecting at least one of a deformation vibration generated in the measurement pipe depending on the mass flow rate and a vibration at (of) the resonant frequency of the first vibration mode of the measurement pipe; and a second vibration detector, provided around an antinode of the second vibration mode of the measurement pipe, for detecting a vibration at the resonant frequency of the second vibration mode of the measurement pipe.

The second vibration type measuring instrument comprises; the measurement pipe; a first vibration detector for detecting at least one of a deformation vibration generated in the measurement pipe depending on the mass flow rate and a vibration at the resonant frequency of the first vibration mode of the measurement pipe; and a second vibration detector, provided around a node of the first vibration mode of the measurement pipe, for detecting a vibration at the resonant frequency of the second vibration mode of the measurement pipe.

The third vibration type measuring instrument comprises the measurement pipe; a first vibration detector, provided around a node of the second vibration mode of the measurement pipe, for detecting at least one of a deformation vibration generated in the measurement pipe depending on the mass flow rate and a vibration at the resonant frequency of the first vibration mode of the measurement pipe; and a second vibration detector for detecting a vibration at the resonant frequency of the second vibration mode of the measurement pipe.

Each of the above described vibration type measuring instruments may further comprise an additional first vibration detector for detecting at least one of a deformation vibration generated in the measurement pipe depending on the mass flow rate and a vibration at the resonant frequency of the first vibration mode of the measurement pipe. In this case, the additional first vibration detector is provided at a position symmetrical to the first vibration detector with respect to the center of the measurement pipe along the axial direction of the measurement pipe.

Each of the above described vibration type measuring instruments may further comprise another second vibration detector for detecting a vibration at the resonant frequency of the second vibration mode of the measurement pipe. In this case, the additional second vibration detector is provided at a position symmetrical to the second vibration detector with respect to the center of the measurement pipe along the axial direction of the measurement pipe.

Each of the vibration type measuring instruments may further comprise a balance weight with a mass, which is substantially the same as that of the first vibration detector, provided at a position symmetrical to the first vibration detector with respect to the center of the measurement pipe along the axial direction of the measurement pipe.

Each of the vibration type measuring instruments may further comprise a balance weight with a mass, which is substantially the same as that of the second vibration detector, provided at a position symmetrical to the second vibration detector with respect to the center of the measurement pipe along the axial direction of the measurement pipe.

The fourth vibration type measuring instrument according to the present invention comprises; a measurement pipe; and a vibration detector for detecting at least one of a deformation vibration generated in the measurement pipe depending on the mass flow rate and a vibration at the resonant frequency of the first vibration mode of the measurement pipe, and also detecting a vibration at the resonant frequency of the second vibration mode of the measurement pipe.

The vibration detector may be provided in a position corresponding to an antinode or around an antinode of the second vibration mode of the measurement pipe.

The vibration type measuring instrument may further comprise an additional vibration detector for detecting at least one of a deformation vibration generated in the measurement pipe depending on the mass flow rate and a vibration at the resonant frequency of the first vibration mode of the measurement pipe, and also detecting a vibration at the resonant frequency of the second vibration mode of the measurement pipe.

The additional vibration detector may be provided at a position symmetrical to the vibration detector with respect to the center of the measurement pipe along the axial direction of the measurement pipe.

The vibration type measuring instrument may comprise a balance weight with a mass, which is substantially the same as that of the vibration detector, provided at a position symmetrical to the vibration detector with respect to the center of the measurement pipe along the axial direction of the measurement pipe.

The fifth vibration measuring instrument according to the present invention comprises the measurement pipe, and a unit for exciting the measurement pipe using a signal obtained by superposing a first excitation signal having a frequency of the first vibration mode of the measurement pipe on a second excitation signal having a frequency equal to and/or around a resonant frequency of the second vibration mode of the measurement pipe.

The vibration type measuring instrument may further comprise a band pass filter for selectively outputting a signal for use in vibrating the measurement pipe, in which its center frequency is controlled within a band width around the resonant frequency of the second vibration mode of the measurement pipe. The band pass filter may be a switched capacitor filter.

The vibration of the measurement pipe may be performed by sweeping, with respect to time, a frequency of an excitation signal within a frequency range including the resonant frequency of the second vibration mode of the measurement pipe.

The vibration type measuring instrument may further comprise a unit for monitoring the frequency of the first excitation signal for vibrating the measurement pipe in the first mode, and compulsorily setting a center frequency of the band pass filter to a predetermined initial frequency when the frequency of the first excitation signal deviates from a predetermined maximum frequency for the first excitation signal.

The vibration measuring instrument may further comprise a unit for monitoring the frequency of the second excitation signal for vibrating the measurement pipe in the second mode, and compulsorily setting a center frequency of the band pass filter to a predetermined initial frequency when the frequency of the second excitation signal deviates from a predetermined maximum frequency for the second excitation signal.

The vibration measuring instrument may further comprise a unit for monitoring the frequency of the first excitation signal and compulsorily sweeping a center frequency of the band pass filter from a minimum frequency when the frequency of the first excitation signal deviates from a predetermined maximum frequency for the first excitation signal.

The vibration measuring instrument may further comprise a unit for monitoring the second excitation signal and compulsorily sweeping a center frequency of the band pass filter from a minimum frequency when the frequency of the second excitation signal deviates from a predetermined maximum frequency for the second excitation signal.

In this specification, the vibration mode conventionally used in measuring a mass flow rate and density is referred to as a first vibration mode, and the sensor for measuring the vibration in the first vibration mode is referred to as a first vibration detector. On the other hand, the vibration mode used for measuring a frequency ratio is referred to as a second vibration mode, and the sensor for measuring the vibration in the second vibration mode is referred to as a second vibration detector. The first and second vibration detectors may be separately provided or a single vibration detector having functions as a first and second vibration detector may be used. If the single vibration detector is adopted, the number of parts can be reduced, thereby reducing the required cost for the entire system.

If the second vibration detector is provided at the antinode of the second vibration mode, then the amplitude of the vibration is larger than at any other point and a maximum output can be obtained when the resonant frequency of the second vibration mode is measured. Thus, the frequency can be measured with high precision. Particularly, if the vibration measuring instrument is used as a mass flowmeter, then the vibration of the second vibration mode produces interference with the time difference (phase difference) signal for the mass flow rate obtained by the first vibration detector (corresponding to 6a and 6b in the example shown in FIG. 1). Therefore, it is desired that the vibration of the second vibration mode is reduced. To attain this, the second vibration detector is provided at a position of greater amplitude (around the antinode of the second vibration mode) to improve the detection sensitivity, thereby successfully reducing the vibration of the second vibration mode. Since the influence of the first vibration mode becomes smaller if the second vibration detector is provided at a position where the amplitude of the first vibration mode is very small (around the node of the first vibration mode), then the detection sensitivity of the second vibration mode increases.

If the first vibration detector is provided at the node of the second vibration mode, the first vibration mode can be measured with the influence of the second vibration mode reduced. This is particularly effective when the vibration measuring instrument is used as the above described mass flowmeter.

When the vibration measuring instrument is used as a mass flowmeter, it is recommended that the vibration of the measurement pipe is symmetrical about the center in the axial direction because the mass flow rate is measured based on the time difference (phase difference) between the first vibration detectors provided symmetrically about the central point. If the vibration of the measurement pipe is unbalanced between the left and the right portions, then the time difference (phase difference) generated between the first vibration detectors at the right and left positions becomes unbalanced, thereby the measurement characteristics deteriorate with changes in temperature, axial force, fluid density, etc.

Therefore, it is desired that each of the first and second vibration detectors is provided symmetrically with respect to the center along the axial direction of the measurement pipe. If there is a single first or second vibration detector, then a balance weight of an equal weight is provided at the point symmetrical to the detector with respect to the center along the axial direction of the measurement pipe to maintain the symmetry of the measurement pipe.

According to the example shown in FIG. 1, the measurement pipe 2 is excited (vibrated) by the resonant frequency of the first vibration mode through a vibration generator 5 and a drive circuit 8. Since the resonant frequency of the second vibration mode is also measured according to the present invention, the measurement pipe should be vibrated to some extent in the second vibration mode. Therefore, the present invention excites the measurement pipe at the resonant frequency of the second vibration mode through the vibration generator, drive circuit, etc., in addition to the resonant frequency of the first vibration mode. Thus, the resonant frequency of the second vibration mode can be stably measured. Simply trying to measure the resonant frequency of the second vibration mode using the vibration in the naturally-generated second vibration mode does not produce sufficient vibration amplitude or stable measurement.

The present invention has been developed to stably measure both first and second vibration modes by performing excitation through the superposed vibration of the resonant frequency of the first vibration mode and the vibration around the resonant frequency of the second vibration mode. A signal of the single frequency of the resonant frequency of the second vibration mode can be used for the excitation at the resonant frequency of the second vibration mode. The resonant frequency of the second vibration mode can be stably measured at a reasonable cost by using a band pass filter capable of controlling the center frequency or by using a switched capacitor filter as the above described band pass filter. The excitation can be performed through time-sweeping the excitation signal within a frequency range containing the resonant frequency of the second vibration mode. Even if the vibration stops when the center frequency of the band pass filter (BPF) deviates from the excitation frequency of the detecting unit due to an external factor, etc., the vibration can be restarted by naturally or compulsorily sweeping the center frequency of the BPF using the BPF control circuit by monitoring the frequencies of the first and second excitation signals. As a result, the resonant frequencies of the first and second vibration modes can be stably and continuously measured.

In this specification, "around the antinode" refers to positions including the position of the antinode and a position near the antinode which is regarded substantially as the antinode. Similarly, "around the node" refers to positions including the position of the node and a position near the node which is regarded substantially as the node.

DESCRIPTION OF THE PREFERRED EMBODIMENTS

Figure 5:
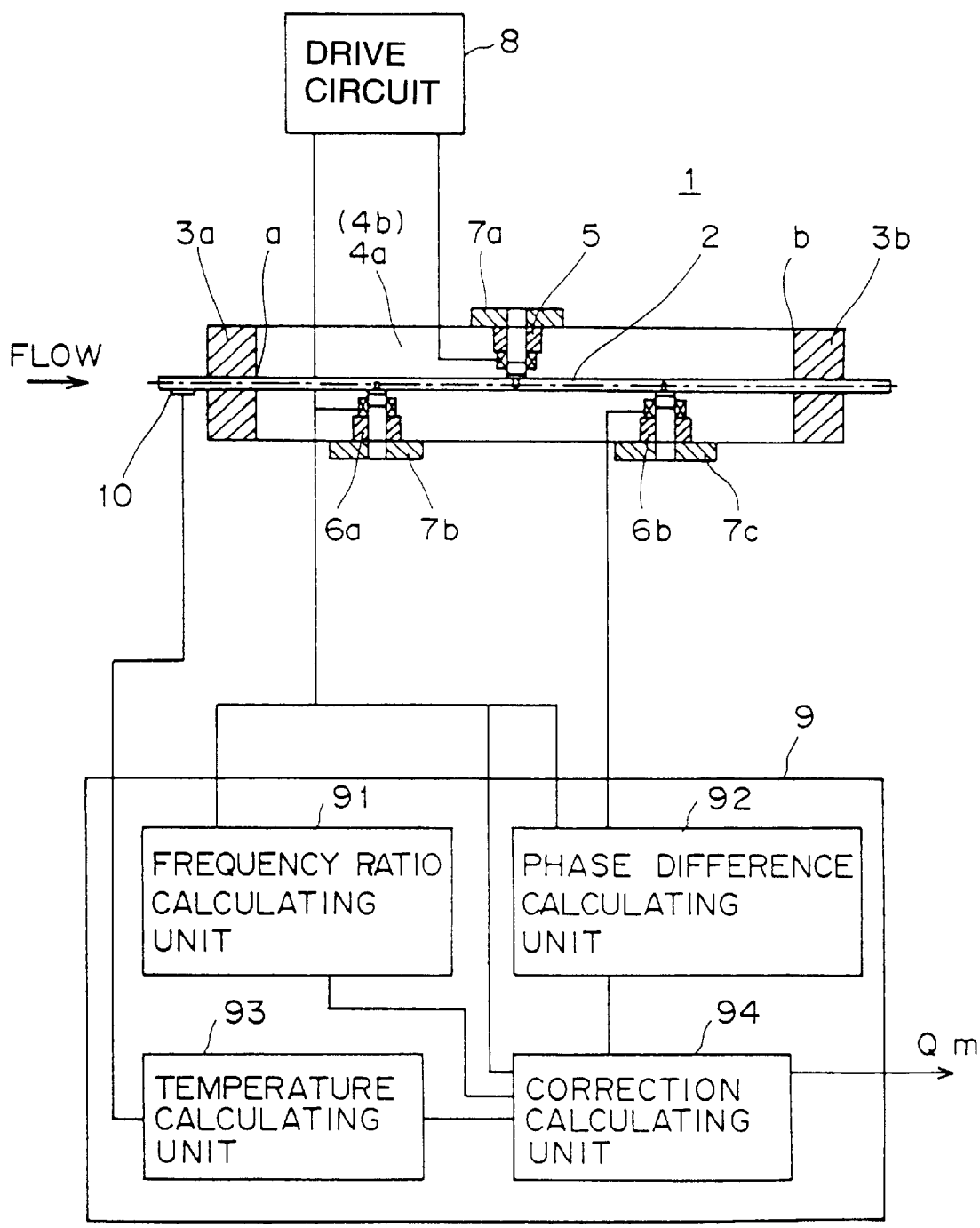
FIG. 5 shows the first embodiment of the vibration type measuring instrument according to the present invention.

FIG. 5 shows the configuration of the vibration type measuring instrument according to the first embodiment of the present invention.

A detecting unit 1 of the vibration type measuring instrument comprises a measurement pipe 2; right and left fixtures 3$a$ and 3$b$ for fixing the node portions a and b of the measurement pipe 2 for the vibration; supporters 4$a$ and 4$b$ (only 4$a$ is shown in FIG. 5) fixed to the fixtures 3$a$ and 3$b$ with screws or by soldering, etc., or designed as being combined with the fixtures 3$a$ and 3$b$ so that the vibrations of the fixtures 3$a$ and 3$b$ cancel each other; and a vibration generator 5, comprising coils fixed to the supporters 4$a$ and 4$b$ by an adapter 7$a$ and a magnet fixed to the central portion of the measurement pipe 2, for vibrating (exciting) the measurement pipe 2 at its resonant frequency.

The detecting unit 1 further comprises speed detecting sensors (or displacement sensors or acceleration sensors) 6$a$ and 6$b$, comprising magnets fixed symmetrically with respect to the vibration generator 5 on the measurement pipe 2, and coils fixed to the supporters 4$a$ and 4$b$ with the adapters 7$b$ and 7$c$, for detecting the vibration of the measurement pipe 2. The vibration type measuring instrument further comprises the drive circuit 8 for outputting a drive signal to the vibration generator 5 so as to keep the amplitude of a signal output from the speed detecting sensor 6$a$ constant, and the signal processing circuit 9 for outputting a mass flow rate signal Qm based on the phase difference (time difference) of the signals from the speed detecting sensors 6$a$ and 6$b$.

Figure 1:
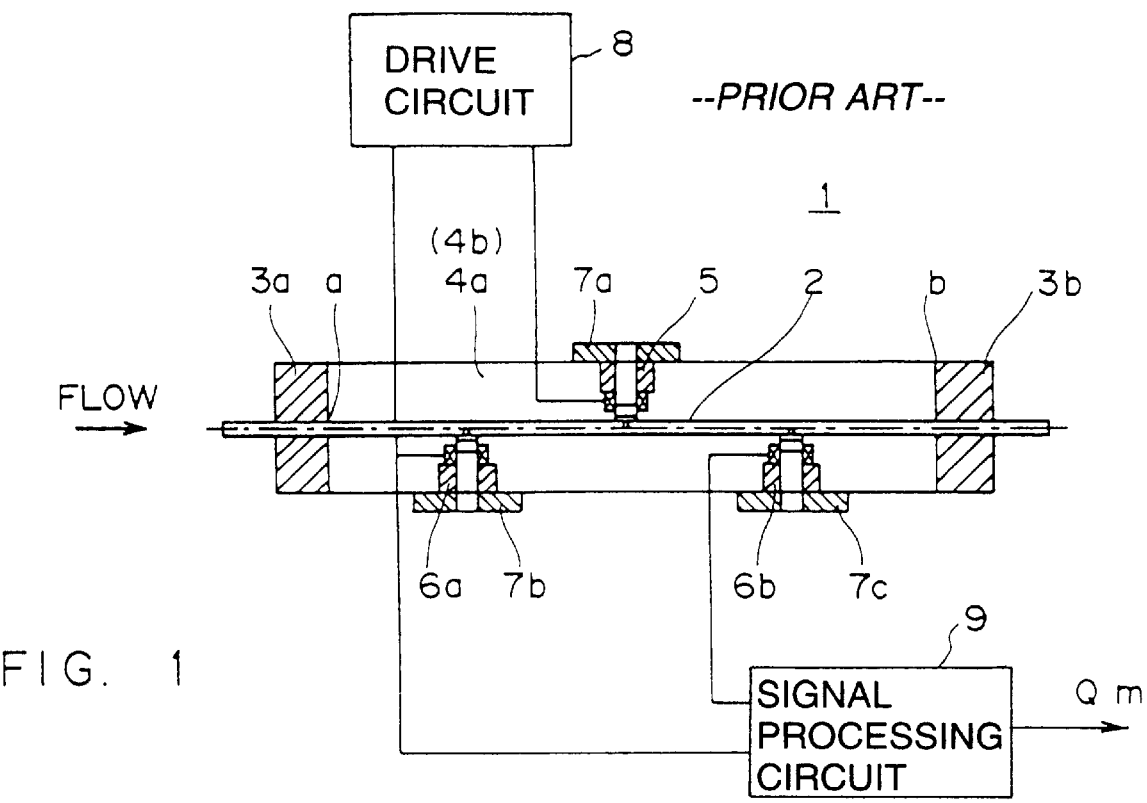
FIG. 1 shows the configuration of an example of a straight pipe type mass flowmeter.
Figure 2:
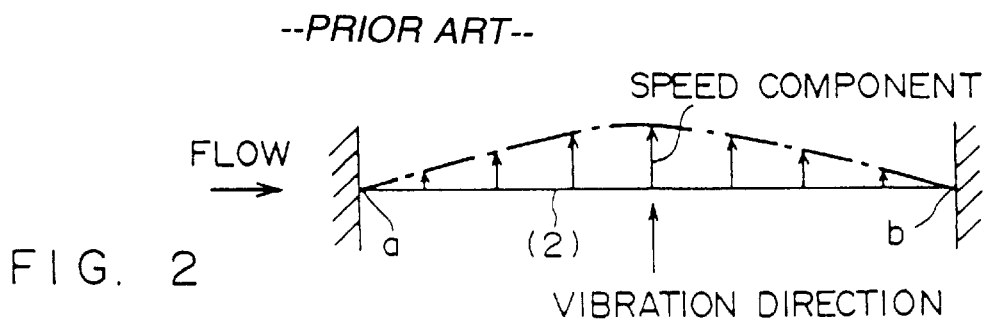
FIG. 2 shows the acceleration working on the fluid.
Figure 3:
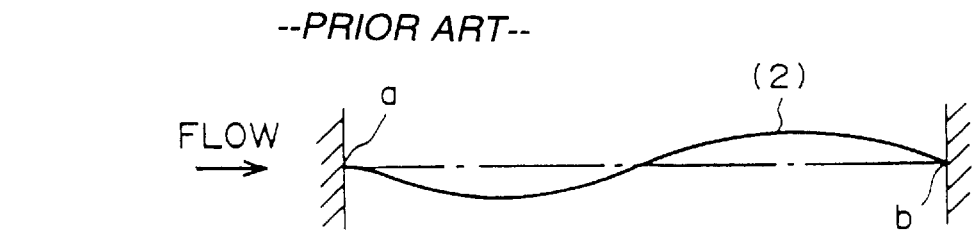
FIG. 3 shows the influence of the fluid reaction working on the measurement pipe.
Figure 4A:
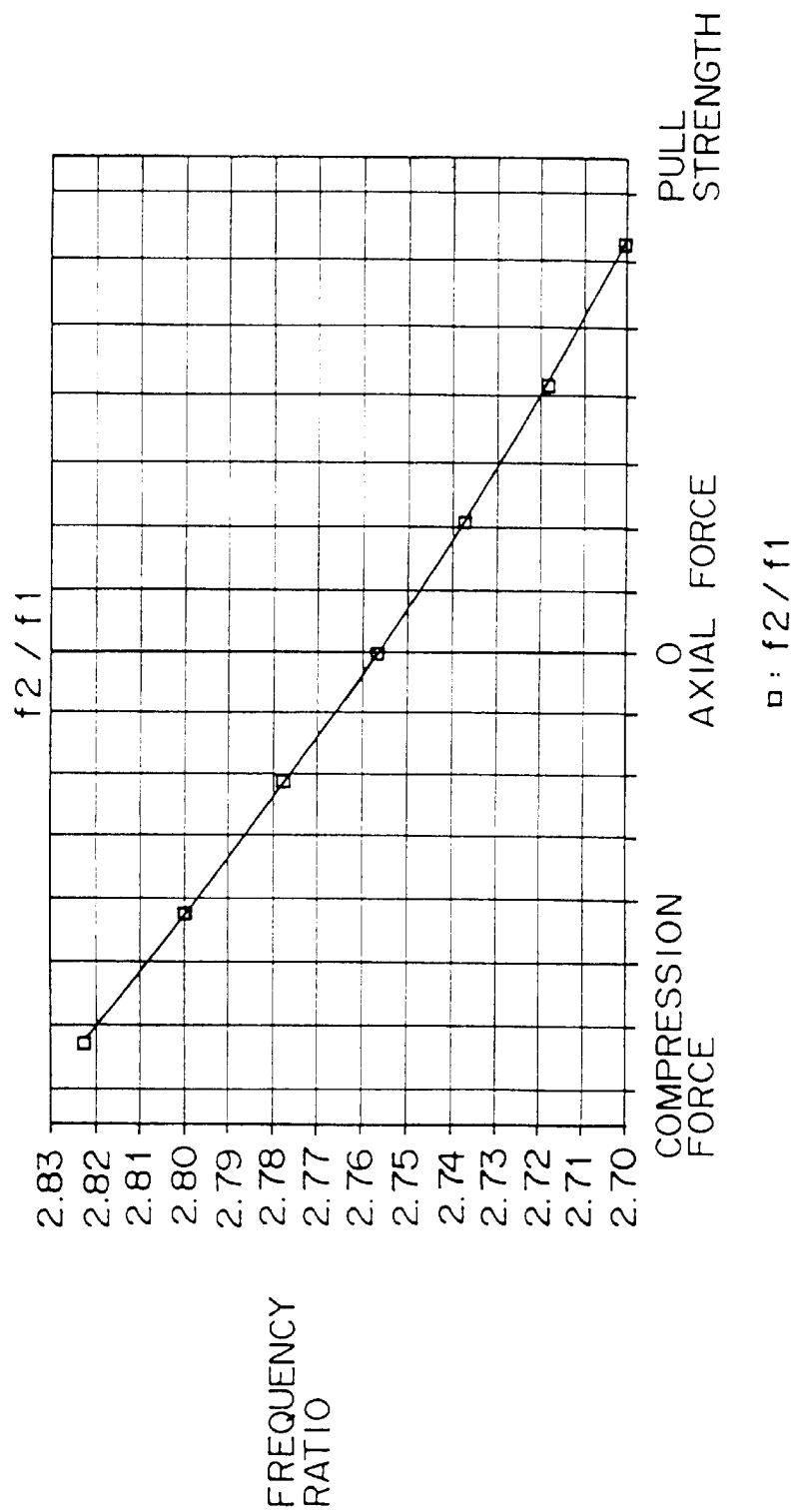
FIGS. 4A and 4B show characteristics for use in explaining the relationship between the axial force of a measurement pipe and the resonant frequency ratio.
Figure 4B:
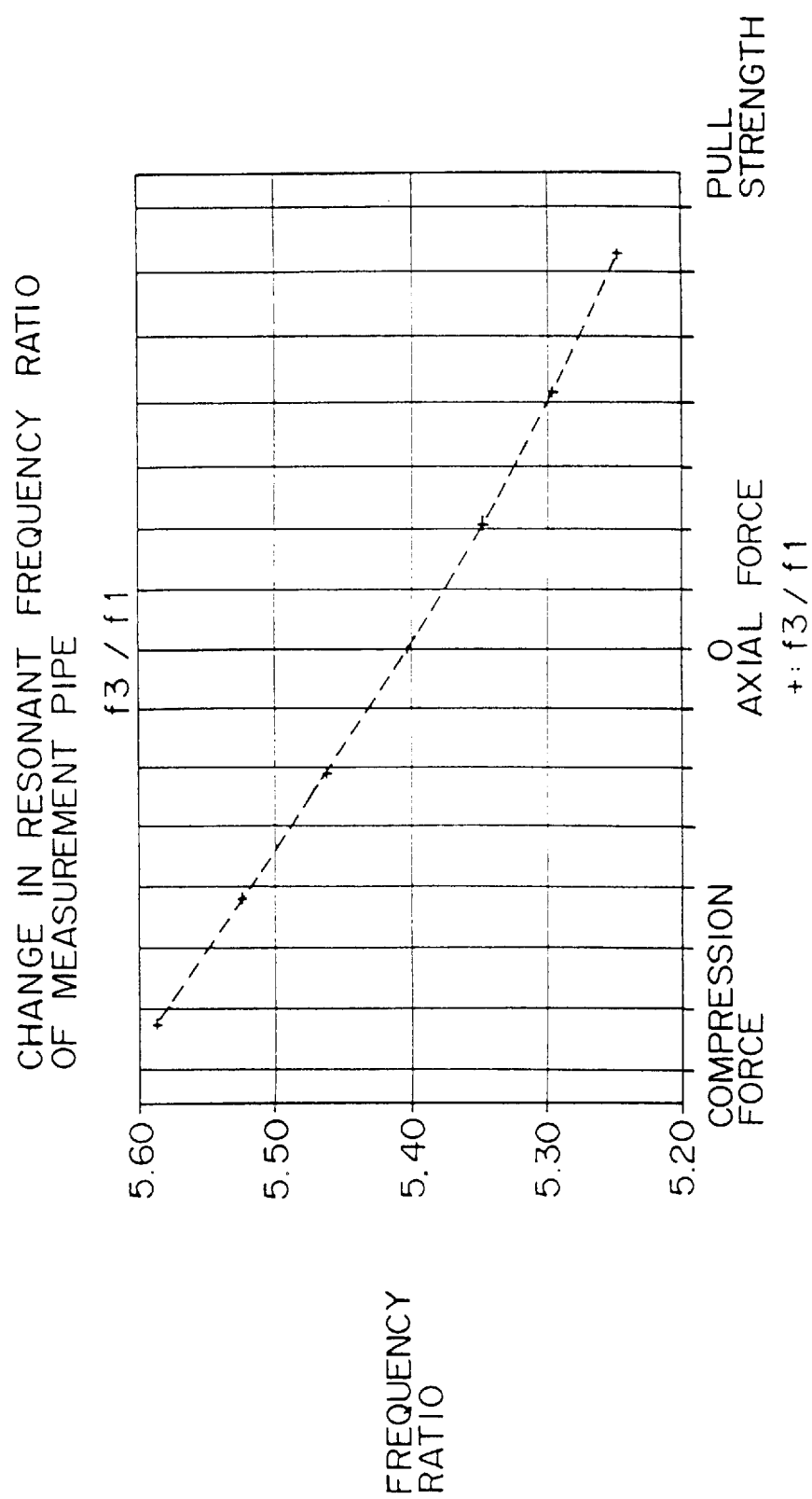

As shown in FIG. 5, the feature of the first embodiment resides in that the speed detecting sensor 6$a$ functions as the first vibration detector and the second vibration detector (corresponding to 6$d$ shown in FIGS. 6 and 7), that the vibration type measuring instrument comprises a temperature sensor 10, and that the signal processing circuit 9 comprises a frequency ratio calculating unit 91, a phase difference calculating unit 92, a temperature calculating unit 93, and a correction calculating unit 94. Other characteristic points are shared with the vibration measuring instrument shown in FIG. 1. The above listed characteristics are described below in detail.

In this example, the drive circuit 8 vibrates the measurement pipe 2 through the vibration generator 5 and speed detecting sensor 6a at around one or both of the resonant frequencies of (in) the first and second vibration modes. At this time, the amplitude of the signal in the first vibration mode in the output from the speed detecting sensor 6a is controlled to be constant according to the drive signal provided from the drive circuit 8 to the vibration generator 5.

The signals from the speed detecting sensors 6a and 6b are input to the phase difference calculating unit 92, in which a signal proportional to the phase difference between the two signals is obtained. The obtained signal is provided to the correction calculating unit 94. The signal from the speed detecting sensor 6a is also input to the frequency ratio calculating unit 91, in which a signal proportional to the ratio of the resonant frequency of the first vibration mode to the resonant frequency of the second vibration mode is obtained, and the result is input to the correction calculating unit 94. The signal from the temperature sensor 10 is converted into a temperature signal by the temperature calculating unit 93 and input to the correction calculating unit 94. The correction calculating unit 94 also directly receives the signal form the speed detecting sensor 6a.

The correction calculating unit 94 receives the outputs from the frequency ratio calculating unit 91, phase difference calculating unit 92, temperature calculating unit 93, and speed sensor 6a, corrects the phase difference signal from the phase difference calculating unit 92 according to the resonant frequency of the first vibration mode of the measurement pipe obtained by the speed sensor 6a, and converts the corrected signal into a tine difference signal. The correction calculating unit 94 corrects the time difference signal according to the temperature signal from the temperature calculating unit 93. Then, the time difference signal is corrected in sensitivity with a change in axial force of the measurement pipe according to the resonant frequency ratio signal from the frequency ratio calculating unit 91, and converted into the flow rate signal Qm, which is then output from the signal processing circuit 9.

Figure 6A:
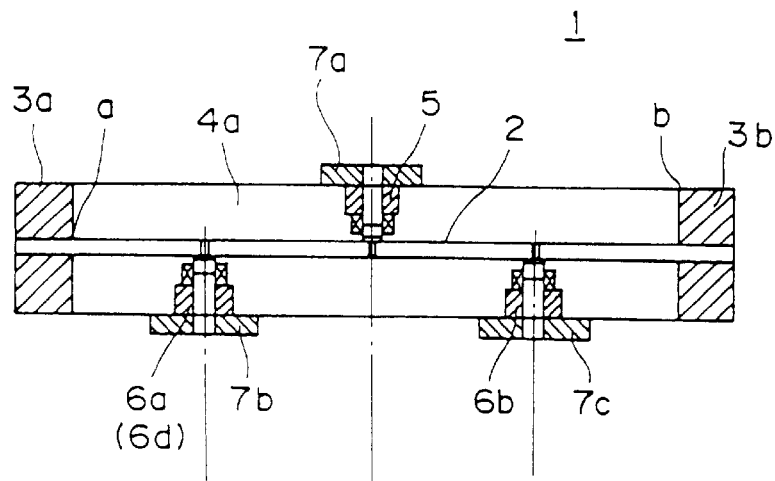
FIG. 6($a$), 6($b$) and 6($c$) show the relationship between the configuration of the detecting unit according to the invention and the deformation of the measurement pipe.
Figure 6B:
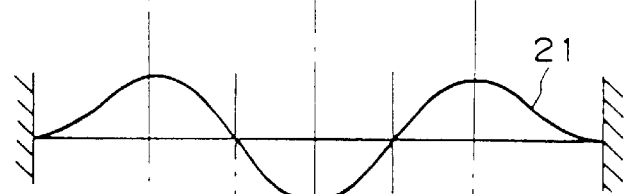
Figure 6C:
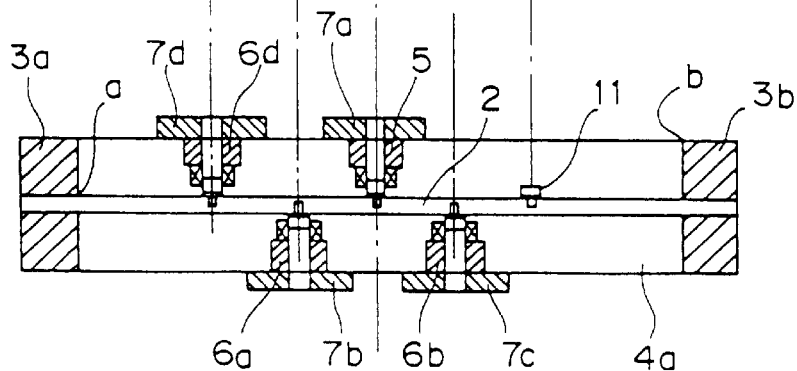

FIG. 6(a), 6(b) and 6(c) show the relationship between the configuration of the detecting unit according to the present invention and the deformation (displacement, or deflection) of the measurement pipe.

FIG. 6(a) exclusively shows the detecting unit 1 shown in FIG. 5. FIG. 6(c) shows an example of the detecting unit 1 including the second speed detecting sensor 6d. FIG. 6(b) shows the deformation of the measurement pipe 2 being vibrated in the transverse direction in the third modes. A curve 21 indicates the deformation of the measurement pipe 2.

In the configuration shown in FIG. 6(a), the speed sensors 6a and 6b are used for detecting the first vibration mode, and the speed sensor 6a is also used for detecting the second vibration mode. In this example, the basic mode is used as the first vibration mode and the third mode is used as the second vibration mode. The speed sensors 6a and 6b are provided symmetrically about the center of the measurement pipe 2 at positions corresponding to the antinodes in the third mode of the measurement pipe 2 (at or around the maximum displacement points of the curve 21). Thus, the vibration of the measurement pipe 2 is well balanced, and the detection sensitivity in the second vibration mode can be improved.

In the configuration shown by FIG. 6(c), the first vibration detectors 6a and 6b are provided at positions corresponding to the nodes of the third mode of the measurement pipe 2 to reduce the influence of the second vibration mode on the measurement for the first vibration mode. Furthermore, a speed detecting sensor 6d (which can be a displacement sensor or an acceleration sensor) is attached as a second vibration detector. It comprises a coil fixed to the supporters 4a and 4b through the adapter 7d and a magnet fixed to the measurement pipe 2, and detects the vibration of the measurement pipe 2. The sensor 6d is provided at a position corresponding to an antinode of the third mode of the measurement pipe 2 to improve the detection sensitivity of the second vibration mode. A balance weight 11 having a mass equal or similar to that of the magnet of the sensor 6d or that of the sensor 6d is mounted symmetrically to the sensor 6d about the center of the measurement pipe 2, and keeps the vibration of the measurement pipe 2 well balanced.

FIG. 7 shows the relationship between another embodiment of the detecting unit 1 according to the present invention and the deformation of the measurement pipe. In this example, the third mode is used as the first vibration mode while the basic mode is used as the second vibration mode.

Figure 7A:
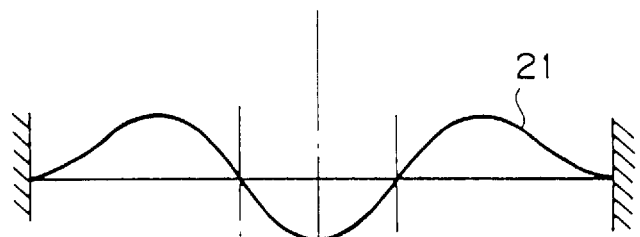
FIG. 7($a$) and 7($b$) show the relationship between another embodiment of the detecting unit according to the invention and the deformation of the measurement pipe.

FIG. 7(a) is a graph indicating the deformation of the measurement pipe 2 being vibrated in the transverse direction in the third mode. The curve 21 shows the deformation of the measurement pipe 2.

Figure 7B:
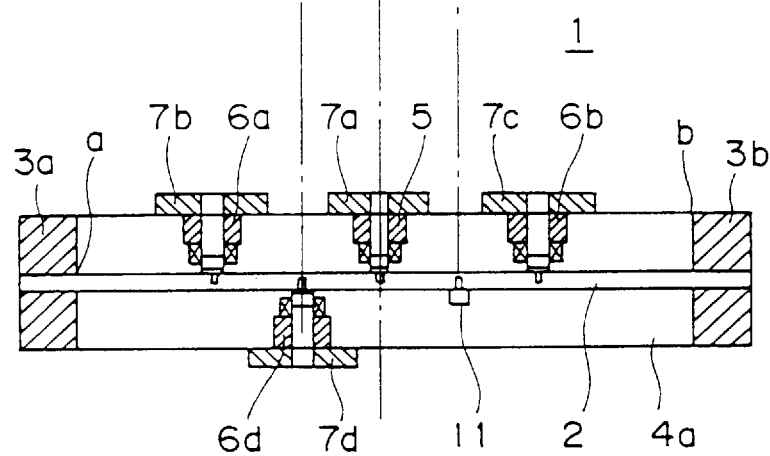

FIG. 7(b) shows the configuration of the detecting unit. A speed detecting sensor 6d (which can be a displacement sensor or an acceleration sensor) is attached as the second vibration detector. It comprises a coil fixed to the supporters 4a and 4b through the adapter 7d and a magnet fixed to the measurement pipe 2, and detects the vibration of the measurement pipe 2. The sensor 6d is provided at a position corresponding to the node of the third mode of the measurement pipe 2 to avoid the undesired influence of the first vibration mode in detecting the second vibration mode. A balance weight 11 having a mass equal or similar to that of the magnet of the sensor 6d or that of the sensor 6d is mounted symmetrically to the sensor 6d about the center of the measurement pipe 2, and keeps the vibration of the measurement pipe 2 well balanced.

Figure 8:
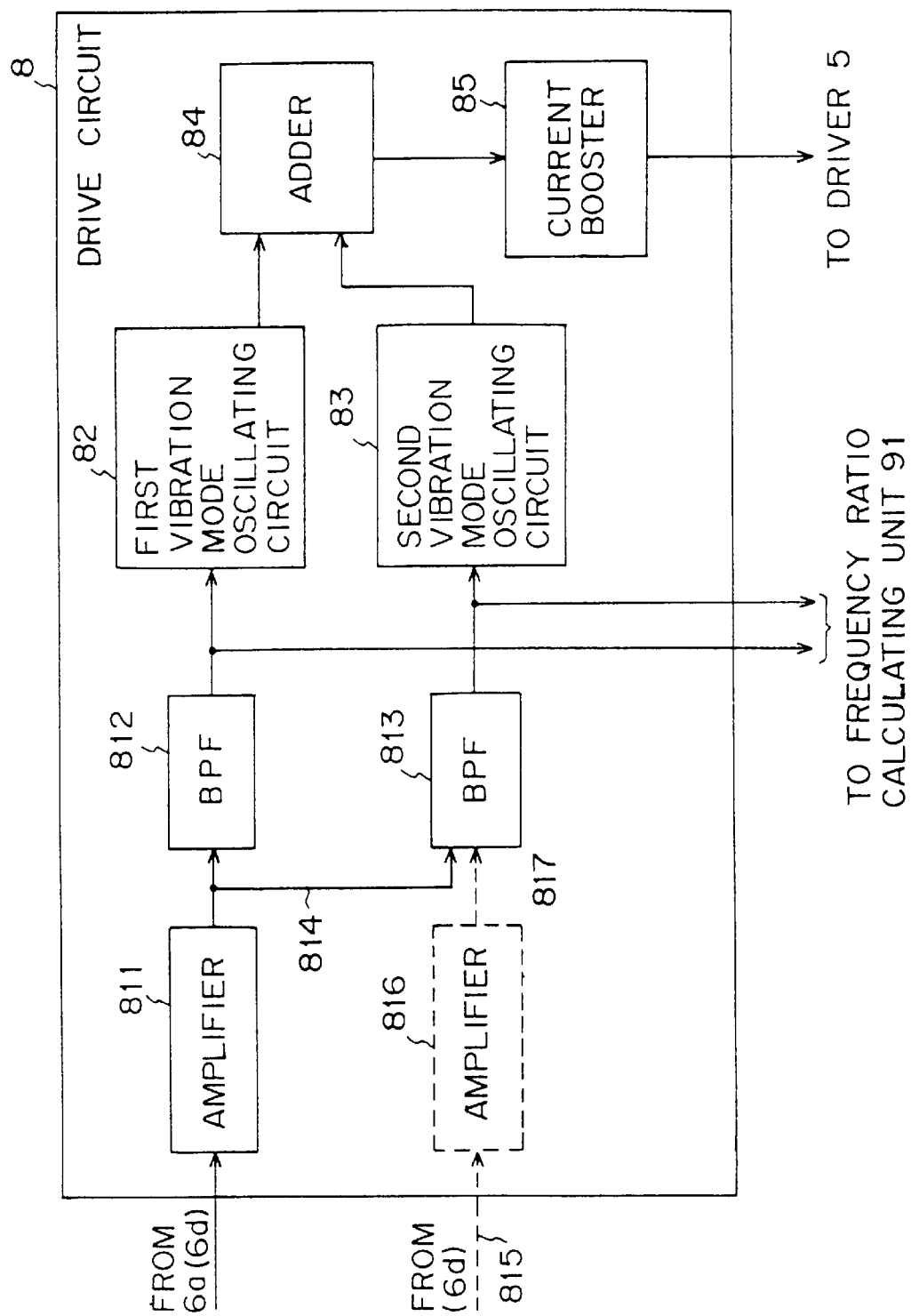
FIG. 8 is a block diagram showing the configuration of the drive circuit according to the embodiment of the present invention.

FIG. 8 is a block diagram showing a configuration example of a drive circuit, which superposes the excitation signal with the resonant frequency of the first vibration mode and the excitation signal with a frequency at (of) or around the resonant frequency of the second vibration mode, and vibrates or excites the measurement pipe 2. The excitation at or around the resonant frequency of the second vibration mode is performed by a single signal having the resonant frequency of the second vibration mode. In FIG. 8, 811 and 816 are amplifiers; 812 and 813 are band pass filters (BPF); 82 is a first vibration mode oscillating circuit; 83 is a second vibration mode oscillating circuit; 84 is an adder; 85 is a current booster.

The amplifier 811 in FIG. 8 amplifies a signal output from the speed detecting sensor 6a for impedance conversion. A path 815, an amplifier 816, and a path 817 are used only when the speed detecting sensor 6d as a second vibration detector is provided in addition to the first vibration detector. In this case, the BPF 813 receives a signal from the path 817, and a path 814 is not used. The amplifiers 816 and 811 function similarly. On the other hand, when the speed detecting sensor 6a functions as both first and second vibration detectors as shown in FIG. 5, none of the path 815, amplifier 816, and path 817 are used, but a signal is input from the path 814 to the BPF 813.

The BPF 812 removes a signal at the frequency of the second vibration mode, and outputs only the signal at the frequency of the first vibration mode to the first vibration mode oscillating circuit 82. On the other hand, the BPF 813 removes a signal at the frequency of the first vibration mode, and outputs only the signal at the frequency of the second vibration mode to the second vibration mode oscillating circuit 83. The first vibration mode oscillating circuit 82 and the second vibration mode oscillating circuit 83 have the same basic structure, and are different only in a circuit constant depending on the difference in oscillation frequency.

Figure 9:
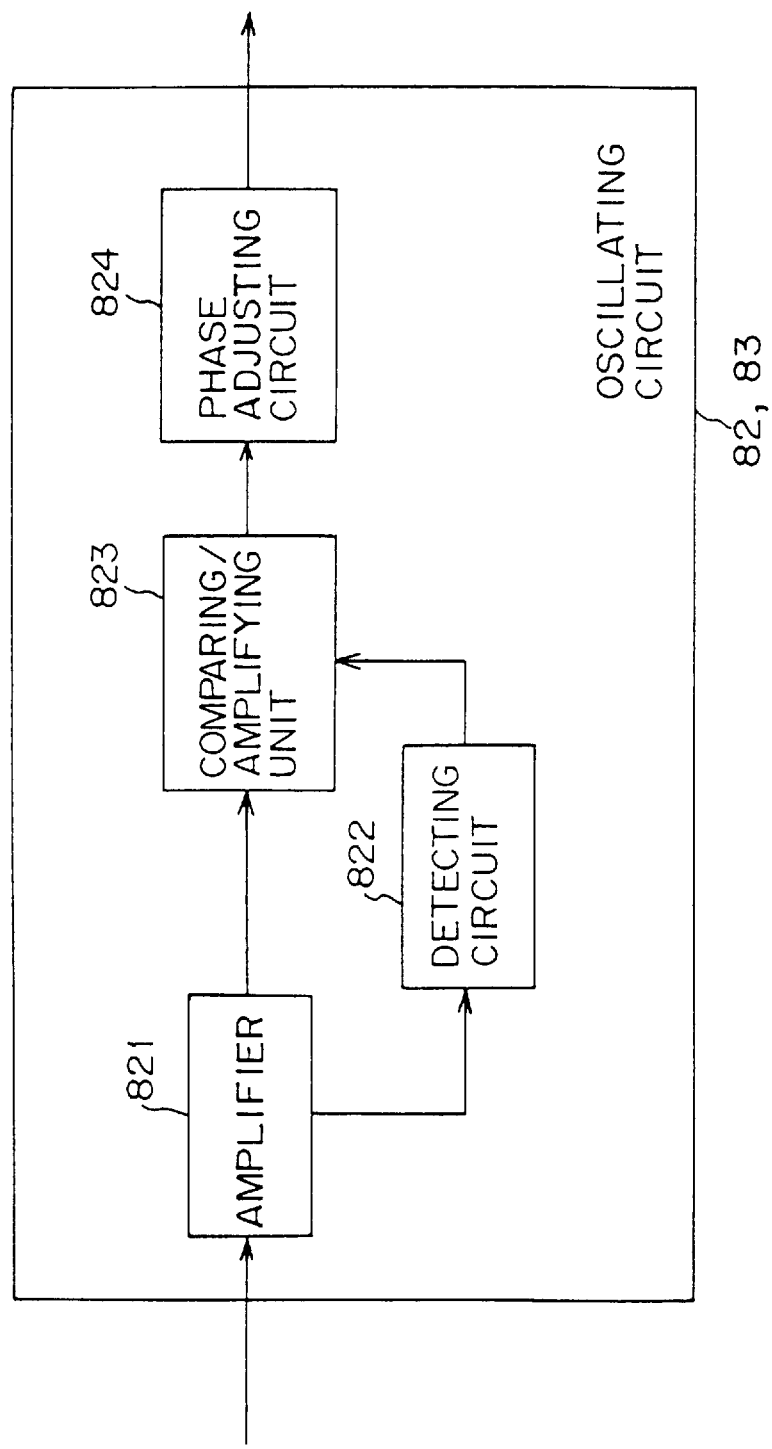
FIG. 9 shows the configuration of the vibration mode generating circuit according to the embodiment of the present invention.

FIG. 9 shows the configuration of the first vibration mode oscillating circuit 82 and second vibration mode oscillating circuit 83. In FIG. 9, 821 is an amplifier; 822 is a detecting circuit; 823 is a comparing/amplifying unit; and 824 is a phase adjusting circuit.

The amplifier 821 amplifies an input signal for impedance-converting, and the output is provided for the detecting circuit 822 and comparing/amplifying unit 823. The detecting circuit 822 detects the amplitude of the input signal, and the detection result is provided to the comparing/amplifying unit 823. The comparing/amplifying unit 823 adjusts and outputs the amplitude of the signal (sine wave) received from the amplifier 821 so that the amplitude of the signal transmitted from the detecting circuit 822 is held constant. The output from the comparing/amplifying unit 823 is transmitted to the phase adjusting circuit 824, shifted in phase, and then transmitted to the adder 84 shown in FIG. 8.

The adder 84 adds up the outputs from the first vibration mode oscillating circuit 82 and second vibration mode oscillating circuit 83, and transmits to a current booster 85 a signal obtained by superposing the frequency of the second vibration mode on the frequency of the first vibration mode. The current booster 85 feeds an electric current proportional to the input signal to the vibration generator (driver) 5. The measurement pipe 2 is vibrated depending on the electric current, and the vibration is detected by the speed detecting sensors 6a, 6b, and 6d transmitted to the drive circuit 8.

As described above, the detecting unit 1 and the drive circuit 8 form a closed loop oscillating system. The first vibration mode and second vibration mode can be concurrently and simultaneously generated by setting the frequency band of the loop using the combination of the BPF 812 and BPF 813 and by adjusting the phase delay by the phase adjusting circuit 824 in the vibration mode oscillating circuits 82 and 83. Thus, the excitation in which the resonant frequencies of the first and second (single) vibration modes are superposed, can be performed. The excitation force of the vibration driver 5 is adjusted by adjusting the amplitude of the output signal by the comparing/amplifying unit 823 such that the signal amplitudes of the first and second vibration modes are kept constant. The frequency ratio is obtained by transmitting the outputs of the BPFs 812 and 813 to the frequency ratio calculating unit 91 shown in FIG. 5 and by individually counting the output values.

Figure 10:
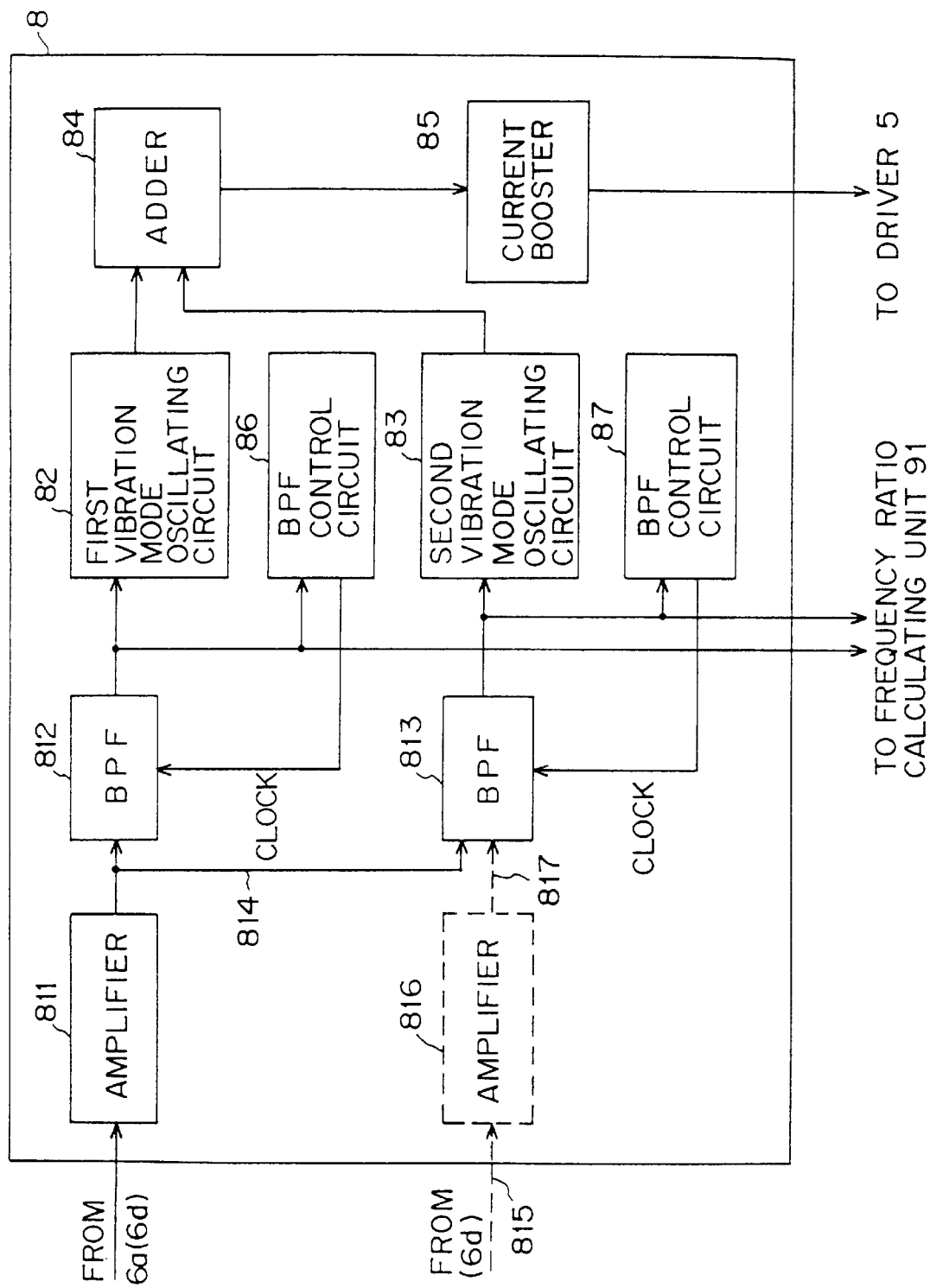
FIG. 10 shows the second drive circuit according to the embodiment of the present invention.

FIG. 10 shows another example of the drive circuit according to the present invention.

The drive circuit is obtained by adding BPF control circuits 86 and 87 to the drive circuit shown in FIG. 8. The center frequencies of the BPFs 812 and 813 are set by the BPF control circuits 86 and 87, respectively. However, if the second vibration mode signal is sufficiently smaller than the first vibration mode signal, the BPF 812 can be omitted. Similarly, if the first vibration mode signal is sufficiently smaller than the second vibration mode signal, the BPF 813 can be omitted.

Figure 11:
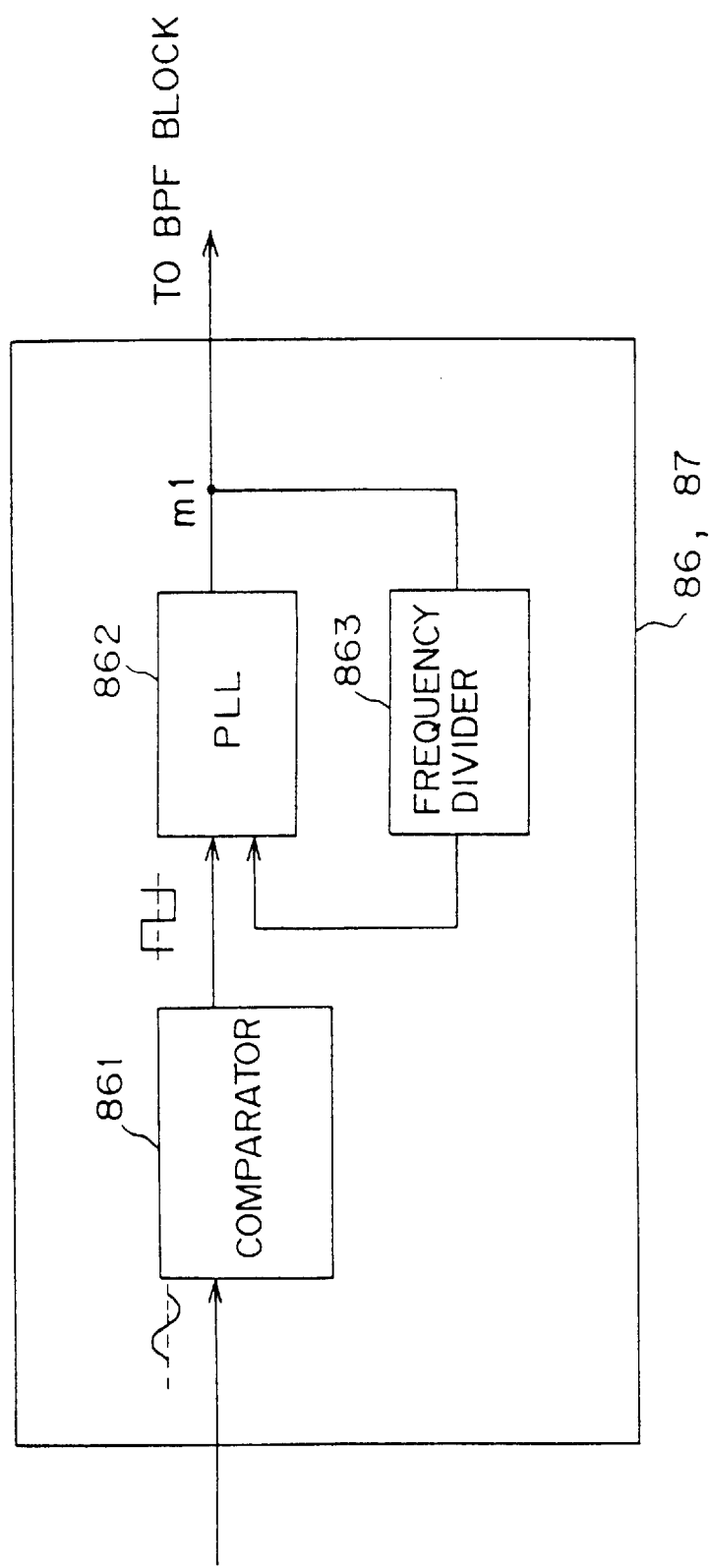
FIG. 11 is a block diagram showing an example of a configuration of the BPF control circuit.

FIG. 11 shows an example of the configuration of the BPF control circuits 86 and 87.

As shown in FIG. 11, each of the BPF control circuits 86 and 87 comprises a comparator 861, a PLL (phase locked loop circuit) 862, and a frequency divider 863. The comparator 861 receives a signal (sine wave) at the frequency of the second vibration mode, converts the input signal into a square wave of the same frequency, and outputs it to the PLL 862. The PLL 862 and the frequency divider 863 form a frequency multiplying circuit.

Figure 12:
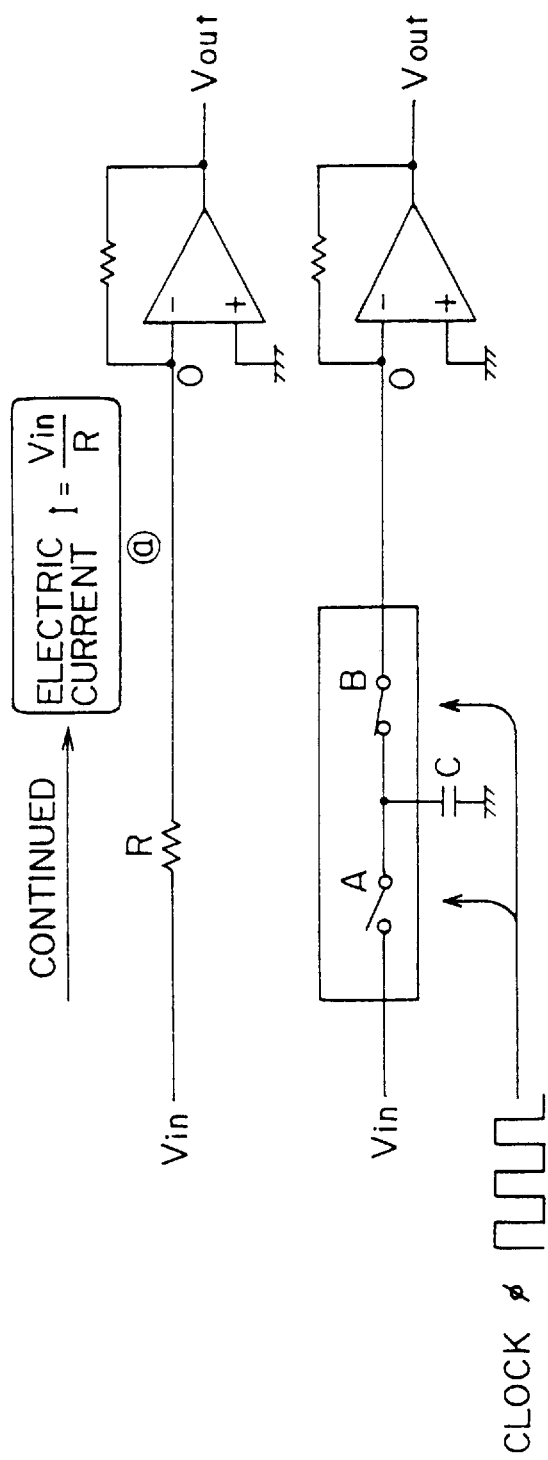
FIG. 12 shows the principle of the switched capacitor filter.

The PLLs 862 and 863 may be, for example, switched capacitor filters. FIG. 12 shows the principle of the switched capacitor filter. The switched capacitor filter is well-known as a filter according to the method for simulating a resistance using the clock frequency ($\phi$) and the built-in capacitor. Therefore, the center frequency can be varied by changing the clock frequency. When the ratio of the clock frequency to the center frequency is m1 and the dividing rate of the divider 863 is m1, the frequency of the output of the PLL 862 shown in FIG. 11 becomes m1 times as high as the input. Therefore, the output frequency of the BPFs 812 and 813 can be set to the resonant frequencies of the first and second vibration modes by entering the output of the PLL 862 as the clock signal for the BPFs 812 and 813.

Figure 13:
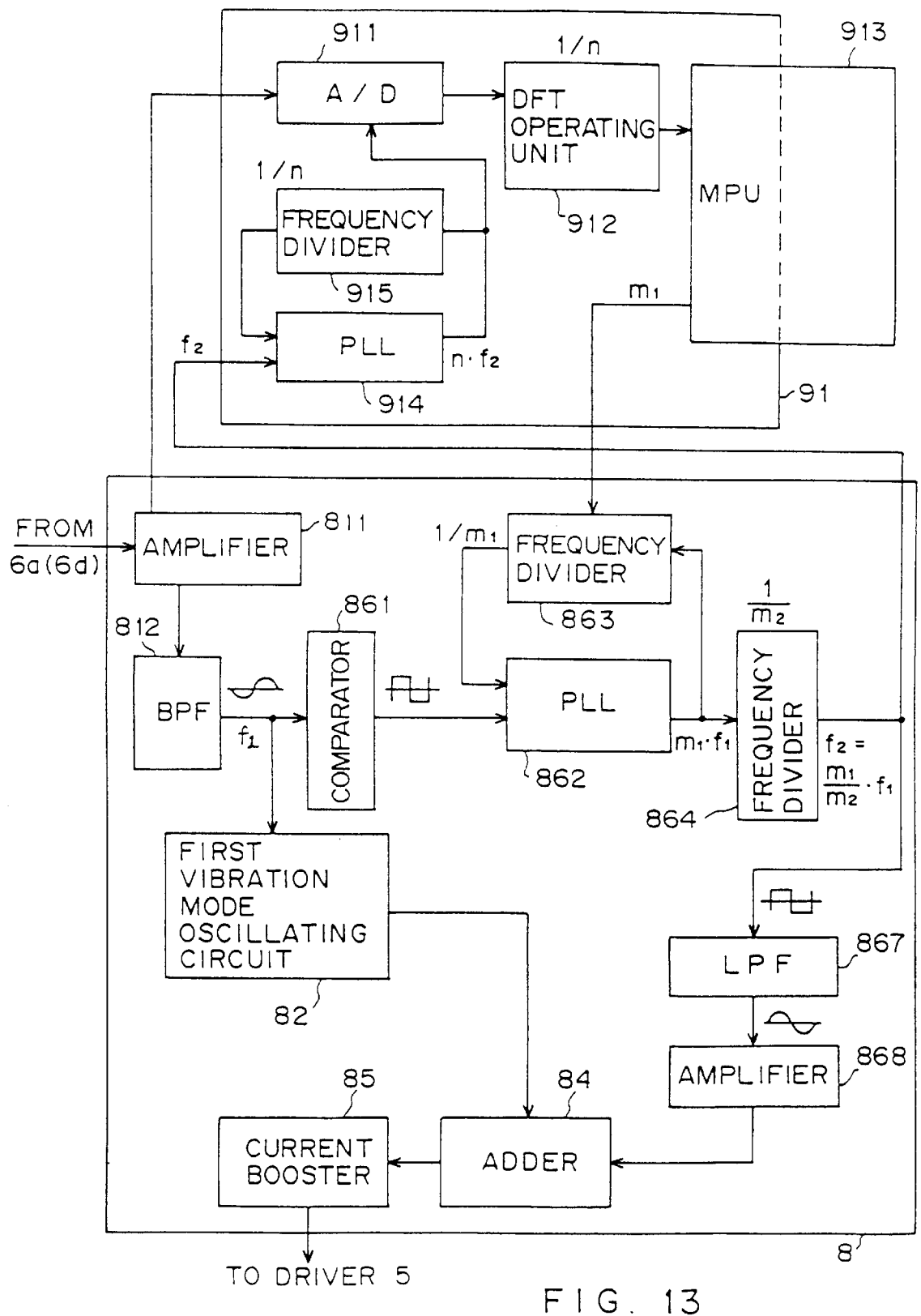
FIG. 13 is a block diagram showing the drive circuit and frequency ratio computing unit according to the embodiment of the present invention.

FIG. 13 is a block diagram showing examples of the frequency ratio calculating unit 91 and the drive circuit 8, which superposes a signal of the resonant frequency of the first vibration mode on a signal of or around the resonant frequency of the second vibration mode for vibrating the measurement pipe 2. The drive circuit 8 is designed by adding the comparator 861, PLL 862, frequency dividers 863 and 864, a low-pass filter (LPF) 867, and an amplifier 868 to the drive circuit shown in FIG. 8. The frequency ratio calculating unit 91 comprises an analog/digital (A/D) converter 911; a discrete Fourier transform operating unit (DFT operating unit) 912; a microprocessor unit (MPU) 913; a PLL 914; and a frequency divider 915.

In the present embodiment, the excitation at (of) or around the resonant frequency of the second vibration mode is performed through a time-sweeping a signal within the frequency range including the resonant frequency of the second vibration mode. First, the output from the sensor 6a is transmitted to the amplifier 811. In this example, the sensor 6a functions as both the first and second detecting units. The amplifier 811 functions as described above, and the output is provided to the BPF 812 and the frequency ratio calculating unit 91.

The BPF 812 functions as described above, that is, it removes the signal around the frequency of the second vibration mode, and outputs only the signal at the frequency of the first vibration mode. The output is transmitted to the comparator 861 and first vibration mode oscillating circuit 82. The first vibration mode oscillating circuit 82 functions as that shown in FIG. 8, and stably vibrates the measurement pipe 2 in the first vibration mode.

The comparator 861 converts an input signal (sine wave) at the frequency of the first vibration mode into a square wave having the same frequency, and outputs it to the PLL 862. The PLL 862 and the frequency divider 863 form a frequency multiplying circuit. When the dividing rate of the frequency divider 863 is m1, the output has a frequency m1 times as high as the input frequency. The dividing rate m1 of the frequency divider 863 can be set by the MPU 913 in the frequency ratio calculating unit 91.

After the frequency of a signal is increased m1 times as high as the input frequency, it is further multiplied 1/m2 times by the frequency divider 864. Since the output of the frequency divider 864 is a square wave, the LPF 867 removes any harmonics to convert the wave into a sine wave at a fundamental frequency. Then, the amplifier 868 amplifies and impedance-converts the signal, and the signal is input to the adder 84 as an excitation signal of the second vibration mode. The adder 84 and current booster 85 function as shown in FIG. 8.

Assuming that the frequency of the first vibration mode is f1, the frequency f1 of the excitation signal of the second vibration mode becomes f1·m1/m2. If m1 is time-swept by the MPU 913, then f2 is also time-swept. The sweeping range of f2 should be set to be broad enough to include the resonant frequency of the second vibration mode, but not to include the resonant frequency of another vibration mode or prolong the time required for the sweeping. The frequency resolution for the sweeping is represented by f1·1/m2. Thus, the time-sweeping is performed around the excitation frequency of the second vibration mode.

Described below is the frequency ratio calculating unit 91.

The frequency ratio calculating unit 91 receives the output from the sensor 6a amplified and impedance-converted by the amplifier 811, and the output from the frequency divider 864 having the excitation signal frequency f2 of the second vibration mode. The output from the divider 864 having the frequency f2 is input to the frequency multiplying circuit comprising the PLL 914 and frequency divider 915. The frequency is multiplied by n in this circuit.

Using this n-times frequency n·f2 as a sampling clock, the A/D converter 911 converts the output from the amplifier 811 into a digital value and transmits it to the DFT operating unit 912. The DFT operating unit 912 computes the signal amplitude of the 1/n frequency component of the sampling frequency. Therefore, the amplitude of the signal component of the frequency f2 of the excitation signal in the second vibration mode is obtained. The obtained signal amplitude value is provided to the MPU 913.

Since the signal amplitude to be transmitted to the MPU 913 is set in a way that the sweep range of f2 contains the resonant frequency of the second vibration mode but does not contain the resonant frequency of other vibration modes, the amplitude indicates a maximum value when f2 is closest to the resonant frequency of the second vibration mode. Therefore, the MPU 913 can obtains the frequency ratio f2/f1 by detecting the value of m1 when the output of the DFT operating unit 912 indicates the maximum value within the sweep range of f2, and by computing m1/m2. At this time, the resolution 1/m2 of the frequency ratio should be set to a value appropriate for correction based on a frequency ratio.

Figure 14:
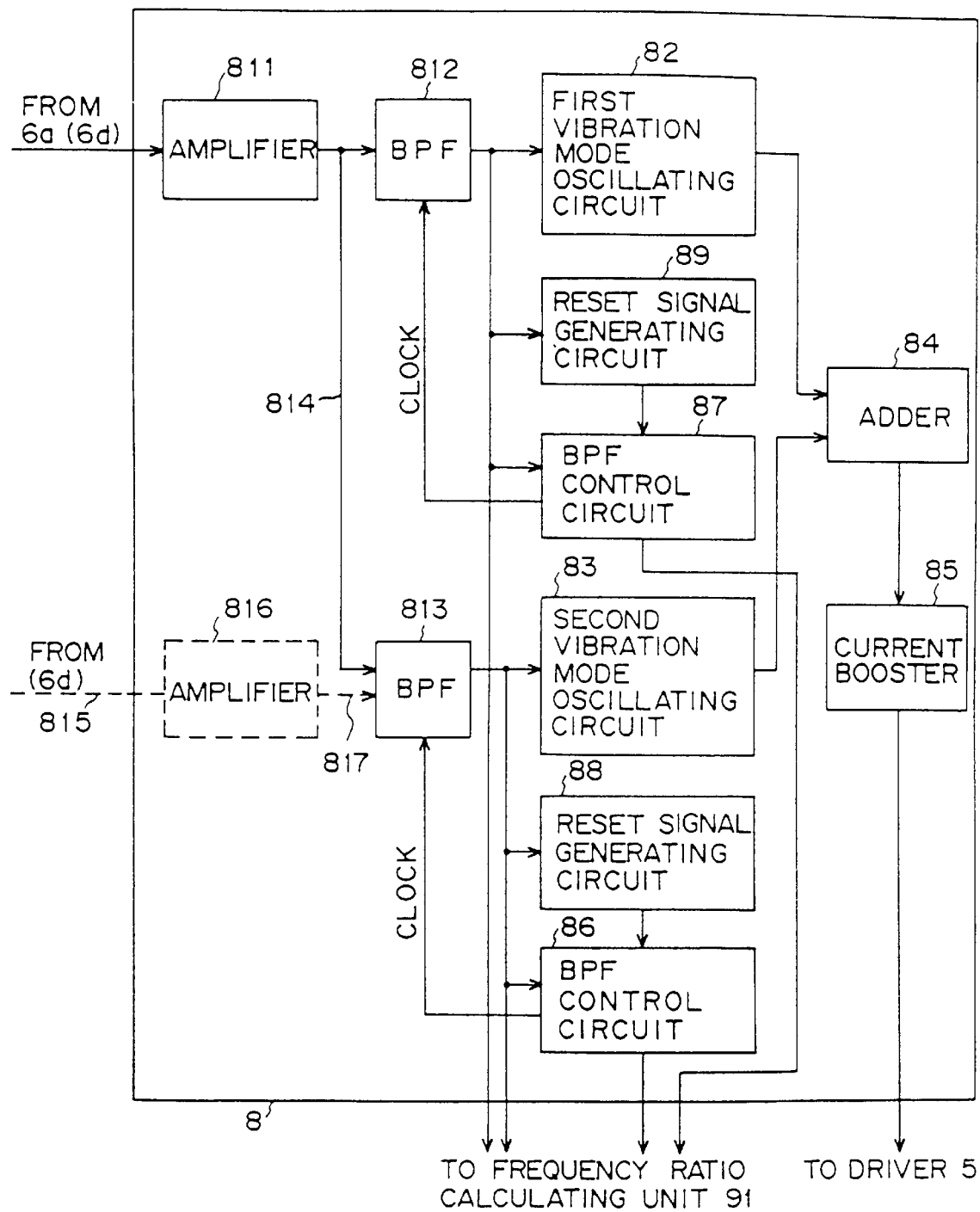
FIG. 14 shows the third drive circuit according to the embodiment of the present invention.

FIG. 14 shows the third drive circuit according to the present embodiment. The drive circuit is an example of a variation of the drive circuit shown in FIG. 10.

The drive circuit functions as the drive circuit 8. In this example, the excitation around the resonant frequency of the second vibration mode is performed by a single vibration signal. The feature of this embodiment resides in that reset signal generating circuits 88 and 89 are added to the drive circuit shown in FIG. 10, and that the outputs of the BPF control circuits 86 and 87 are sent to the frequency ratio calculating unit 91 shown in FIG. 5.

Figure 15:
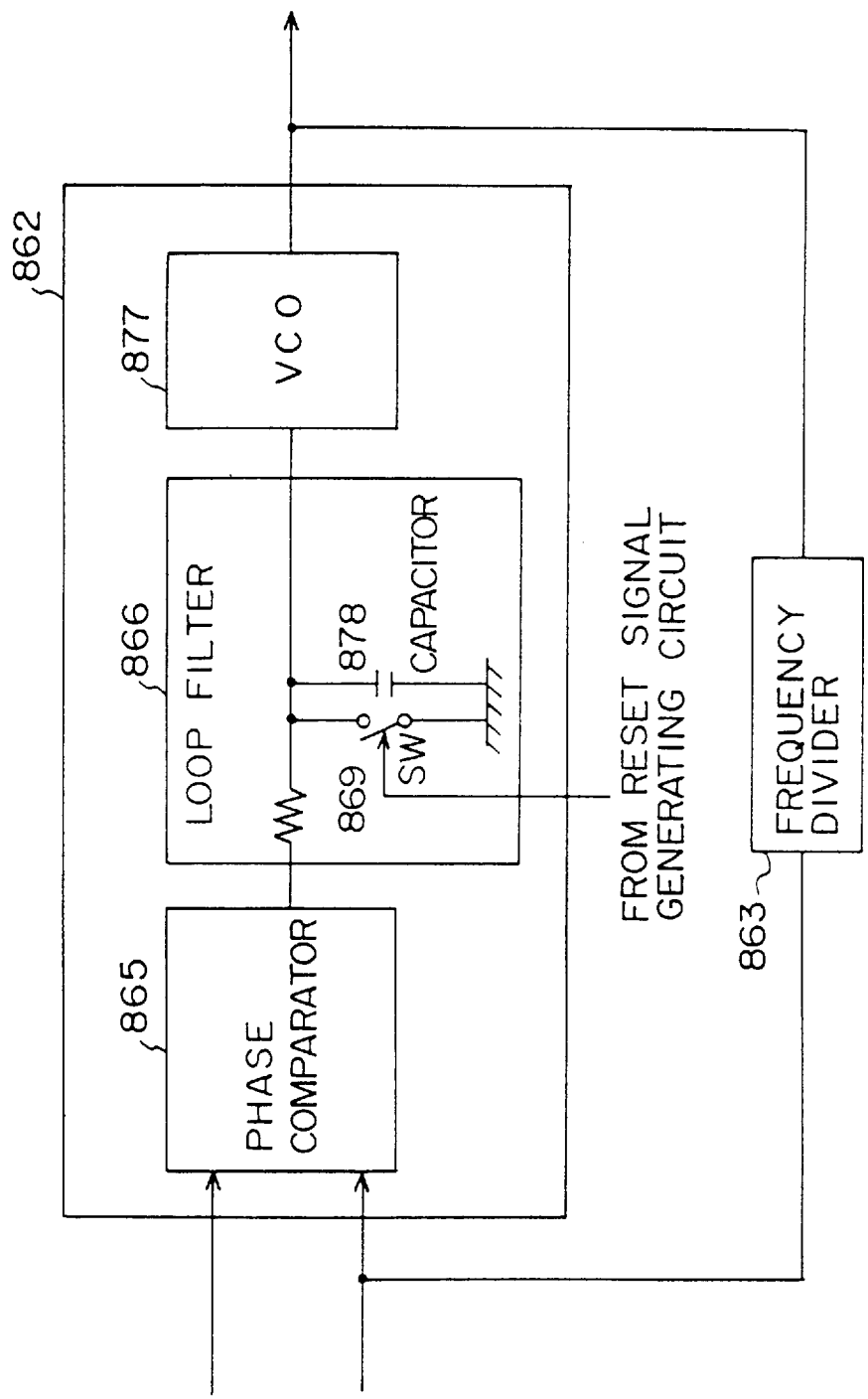
FIG. 15 shows the PLL circuit according to the embodiment of the present invention.

The BPF control circuits 86 and 87 are the same as those shown in FIG. 11. The PLL 862 comprises, as shown in FIG. 15, a phase comparator 865, a loop filter 866, and a VCO (voltage controlled oscillator) 877.

In this case, the output containing the alternating component from the phase comparator 865 is integrated by the loop filter 866 and converted into a direct current voltage. Since the VCO 877 oscillates at a frequency proportional to the direct current, the VCO 877 is controlled such that the phase difference between the input signal of the phase comparator 865 and the output signal of the divider 863 is kept constant. The loop filter 866 comprises a capacitor 878, a switch (SW) 869, etc. When the SW 869 is turned on to discharge the electric charge accumulated by the capacitor 878, the VCO 877 performs a natural sweep from a predetermined minimum frequency to a predetermined maximum frequency.

The reset signal generating circuits 88 and 89 in FIG. 14 control the above described SW 869. The reset signal generating circuits 88 and 89 measure the vibration mode frequency. If the measured frequency reaches the maximum frequency, then a signal instructing a turn-on of the SW 869 is generated. Therefore, the PLL 862 is swept until the vibration is resumed if the oscillation frequency reaches the maximum frequency due to, for example, a suspension of the vibration. The reset signal generating circuits 88 and 89 can be realized by, for example, a computer such as a microcomputer, etc.

Figure 16:
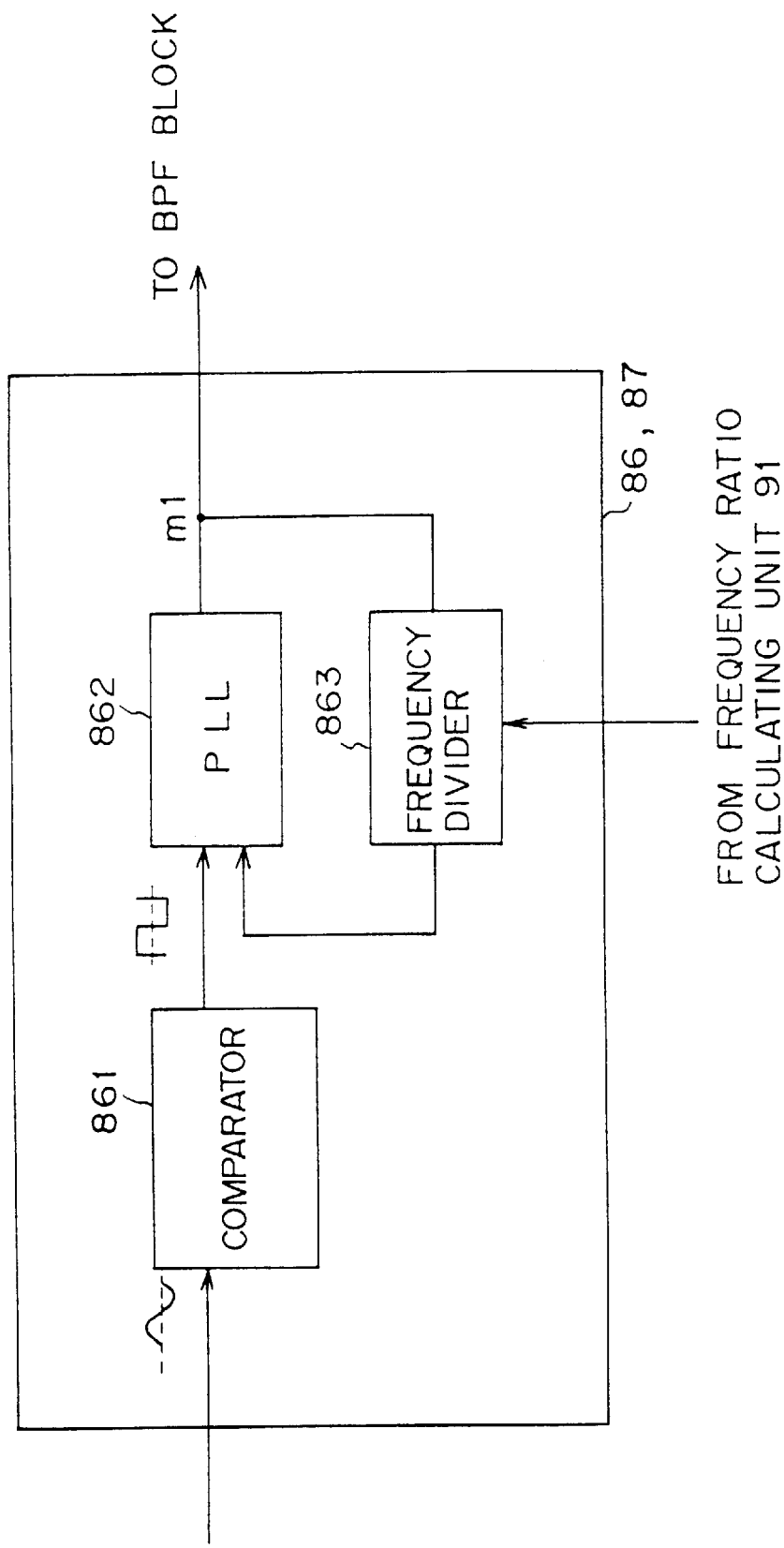
FIG. 16 shows another example of the configuration of the BPF control circuit.

FIG. 16 shows an example of the configuration of the BPF control circuits 86 and 87 used when the center frequency of the BPF is compulsorily swept from the minimum frequency. Like the circuit shown in FIG. 11, the BPF control circuits 86 and 87 comprise the comparator 861, PLL 862, and frequency divider 863, but differ from the one shown in FIG. 11 in that a control signal is received from the frequency ratio calculating unit 91 shown in FIG. 5 to the frequency divider 863.

That is, the frequency divider 863 sets the dividing ratio according to the control signal from the frequency ratio calculating unit 91. The center frequency of the BPF is compulsorily swept from the minimum frequency to the maximum frequency by changing the dividing ratio. During the compulsory sweep, the output of the BPF is monitored by the frequency ratio calculating unit 91. When the output exceeds a predetermined level, the compulsory sweep is stopped and switched into a self-tracking operation.

According to the present invention, the ratio of the resonant frequency of the first vibration mode to the resonant frequency of the second vibration mode is obtained, and the correction of the sensitivity according to the change of the axial force acting on the measurement pipe is performed in addition to the temperature adjustment. Further, the second vibration detector is provided around the antinode of the second vibration mode or around the node of the first vibration mode. Therefore, a correct measurement can be made with enhanced detection sensitivity in the second vibration mode even with a transitional temperature change, without requiring a complicated configuration for the detecting unit and without affecting the stability of the vibration measuring instrument.

If the first vibration detector is provided around the node of the second vibration mode, the influence of the measurement in the second vibration mode on the measurement in the first vibration mode can be reduced. The vibration of a measurement pipe can be kept symmetrical about the center in the axial direction by mounting the first vibration detector and second vibration detector symmetrically about the center in the axial direction of the measurement pipe, and by adding balance weights at positions symmetrical about the center in the axial direction of the measurement pipe when a single first vibration detector or second vibration detector is provided.

Furthermore, the resonant frequency of the second vibration mode can be stably measured by performing excitation through superposing the vibration at the resonant frequency of the first vibration mode and the vibration around the resonant frequency of the second vibration mode.

Even if the vibration stops when the center frequency of the band pass filter (BPF) deviates from the excitation frequency of the detecting unit due to an external factor, etc., the vibration can be restarted by naturally or compulsorily sweeping the center frequency of the BPF by the BPF control circuit by monitoring the frequencies of the first and second excitation signals. As a result, the resonant frequencies of the first and second vibration modes can be stably and continuously measured.

What is claimed is:

1. A vibration type measuring instrument for measuring at least one of a mass flow rate and a density of a fluid flowing through a straight measurement pipe by vibrating the measurement pipe, obtaining a frequency ratio of a resonant frequency of a first vibration mode to a resonant frequency of a second vibration mode of the measurement pipe, and for correcting a measured value of at least one of the mass flow rate and the density according to the frequency ratio, comprising:

said measurement pipe; and means for exciting said measurement pipe using an excitation signal to which a first excitation signal having a frequency of the first vibration mode of said measurement pipe and a second excitation signal having a frequency around a frequency of the second vibration mode of said measurement pipe are superimposed, wherein:

an excitation by said means for exciting is performed by sweeping an excitation signal within a frequency range including the frequency of the second vibration mode.

2. A vibration type measuring instrument for measuring at least one of a mass flow rate and a density of a fluid flowing through a straight measurement pipe by vibrating the measurement pipe, obtaining a frequency ratio of a resonant frequency of a first vibration mode to a resonant frequency of a second vibration mode of the measurement pipe, and for correcting a measured value of at least one of the mass flow rate and the density according to the frequency ratio, comprising:

said measurement pipe;

means for exciting said measurement pipe using an excitation signal to which a first excitation signal having a frequency of the first vibration mode of said measurement pipe and a second excitation signal having a frequency around a frequency of the second vibration mode of said measurement pipe are superimposed;

a band pass filter for selectively outputting a signal for use in vibrating the measurement pipe by controlling a center frequency within a band width around the frequency of the second vibration mode, and means for compulsorily setting a center frequency of said band pass filter to a predetermined initial frequency when the frequency of the first excitation signal deviates from a predetermined maximum frequency for the first excitation signal.

3. The vibration type measuring instrument according to claim 2, wherein said band pass filter is a switched capacitor filter.

4. A vibration type measuring instrument for measuring at least one of a mass flow rate and a density of a fluid flowing through a straight measurement pipe by vibrating the measurement pipe, obtaining a frequency ratio of a resonant frequency of a first vibration mode to a resonant frequency of a second vibration mode of the measurement pipe, and for correcting a measured value of at least one of the mass flow rate and the density according to the frequency ratio, comprising:

said measurement pipe;

means for exciting said measurement pipe using an excitation signal to which a first excitation signal having a frequency of the first vibration mode of said measurement pipe and a second excitation signal having a frequency around a frequency of the second vibration mode of said measurement pipe are superimposed;

a band pass filter for selectively outputting a signal for use in vibrating the measurement pipe by controlling a center frequency within a band width around the frequency of the second vibration mode, and means for compulsorily setting a center frequency of said band pass filter to a predetermined initial frequency when the frequency of the second excitation signal deviates from a predetermined maximum frequency for the second excitation signal.

5. The vibration type measuring instrument according to claim 4, wherein said band pass filter is a switched capacitor filter.

6. A vibration type measuring instrument for measuring at least one of a mass flow rate and a density of a fluid flowing through a straight measurement pipe by vibrating the measurement pipe, obtaining a frequency ratio of a resonant frequency of a first vibration mode to a resonant frequency of a second vibration mode of the measurement pipe, and for correcting a measured value of at least one of the mass flow rate and the density according to the frequency ratio, comprising:

said measurement pipe;

means for exciting said measurement pipe using an excitation signal to which a first excitation signal having a frequency of the first vibration mode of said measurement pipe and a second excitation signal having a frequency around a frequency of the second vibration mode of said measurement pipe are superimposed;

a band pass filter for selectively outputting a signal for use in vibrating the measurement pipe by controlling a center frequency within a band width around the frequency of the second vibration mode, and means for compulsorily sweeping a center frequency of said band pass filter from a minimum frequency when the frequency of the first excitation signal deviates from a predetermined maximum frequency for the first excitation signal.

7. The vibration type measuring instrument according to claim 6, wherein said band pass filter is a switched capacitor filter.

8. A vibration type measuring instrument for measuring at least one of a mass flow rate and a density of a fluid flowing through a straight measurement pipe by vibrating the measurement pipe, obtaining a frequency ratio of a resonant frequency of a first vibration mode to a resonant frequency of a second vibration mode of the measurement pipe, and for correcting a measured value of at least one of the mass flow rate and the density according to the frequency ratio, comprising:

said measurement pipe;

means for exciting said measurement pipe using an excitation signal to which a first excitation signal having a frequency of the first vibration mode of said measurement pipe and a second excitation signal having a frequency around a frequency of the second vibration mode of said measurement pipe are superimposed;

a band pass filter for selectively outputting a signal for use in vibrating the measurement pipe by controlling a center frequency within a band width around the frequency of the second vibration mode, and means for compulsorily sweeping a center frequency of said band pass filter from a minimum frequency when the frequency of the second excitation signal deviates from a predetermined maximum frequency for the second excitation signal.

9. The vibration type measuring instrument according to claim 8, wherein said band pass filter is a switched capacitor filter.

* * * * *